(12) United States Patent
Le et al.

(10) Patent No.: US 11,261,165 B2
(45) Date of Patent: Mar. 1, 2022

(54) TWO PIECE SENSOR ASSEMBLY AND METHOD OF USE

(71) Applicant: MediBeacon Inc., St. Louis, MO (US)

(72) Inventors: Anthony Le, St. Louis, MO (US); Martin Leugers, St. Louis, MO (US)

(73) Assignee: MediBeacon Inc., St. Louis, MO (US)

( * ) Notice: Subject to any disclaimer, the term of this patent is extended or adjusted under 35 U.S.C. 154(b) by 211 days.

(21) Appl. No.: 16/552,539

(22) Filed: Aug. 27, 2019

(65) Prior Publication Data

US 2020/0223805 A1 Jul. 16, 2020

Related U.S. Application Data

(60) Provisional application No. 62/793,000, filed on Jan. 16, 2019.

(51) Int. Cl.
| | | |
|---|---|---|
| *C07D 241/28* | (2006.01) | |
| *A61K 49/00* | (2006.01) | |
| *A61B 5/1455* | (2006.01) | |
| *A61B 5/00* | (2006.01) | |

(52) U.S. Cl.
CPC .......... *C07D 241/28* (2013.01); *A61B 5/1455* (2013.01); *A61B 5/6833* (2013.01); *A61B 5/6835* (2013.01); *A61K 49/0021* (2013.01); *A61B 2562/222* (2013.01)

(58) Field of Classification Search
CPC ... A61B 5/1455; A61B 5/6833; A61B 5/6835; A61B 5/14552; A61B 2562/0233
See application file for complete search history.

(56) References Cited

U.S. PATENT DOCUMENTS

| | | | | |
|---|---|---|---|---|
| 4,494,550 A | * | 1/1985 | Blazek | A61B 5/02416 600/473 |
| 5,584,296 A | | 12/1996 | Cui et al. | |
| 5,817,008 A | * | 10/1998 | Rafert | A61B 5/14552 600/323 |

(Continued)

FOREIGN PATENT DOCUMENTS

| | | |
|---|---|---|
| WO | 2010020673 A2 | 2/2010 |
| WO | 2012112885 A1 | 8/2012 |

(Continued)

OTHER PUBLICATIONS

Brenner et al., "Quantitative Importance of Changes in Postglomerular Colloid Osmotic Pressure in Mediating Glomerulotubular Balance in the Rat," The Journal of Clinical Investigation, vol. 52, (1973), pp. 190-197.

(Continued)

*Primary Examiner* — Eric F Winakur
(74) *Attorney, Agent, or Firm* — Armstrong Teasdale LLP

(57) ABSTRACT

Disclosed herein is a two-piece sensor assembly that includes an attachment collar configured to attach to a body surface of a patient and comprising at least one opening, and a skin sensor configured to seat into the at least one opening in the attachment collar. The skin sensor includes at least one radiation source configured to irradiate the body surface with at least one interrogation light, and at least one detector configured to detect at least one response light incident from the direction of the body surface.

20 Claims, 11 Drawing Sheets

(56) References Cited

U.S. PATENT DOCUMENTS

| | | | | |
|---|---|---|---|---|
| 5,879,373 | A * | 3/1999 | Roper | A61B 5/14552 600/344 |
| 6,381,489 | B1 * | 4/2002 | Ashibe | A61B 5/1455 600/344 |
| 6,619,838 | B2 | 9/2003 | Bencini et al. | |
| 6,839,585 | B2 * | 1/2005 | Lowery | A61B 5/14552 600/344 |
| 6,920,345 | B2 * | 7/2005 | Al-Ali | A61B 5/14552 600/344 |
| 6,925,317 | B1 * | 8/2005 | Samuels | A61B 5/14532 600/309 |
| 6,995,019 | B2 | 2/2006 | Hein et al. | |
| 7,050,175 | B1 | 5/2006 | Freimann et al. | |
| 7,113,815 | B2 * | 9/2006 | O'Neil | A61B 5/14551 600/344 |
| 8,155,000 | B2 | 4/2012 | Vasseur | |
| 8,664,392 | B2 | 3/2014 | Rajagopalan et al. | |
| 8,688,187 | B2 | 4/2014 | Dellostritto et al. | |
| 8,697,033 | B2 | 4/2014 | Poreddy et al. | |
| 8,722,685 | B2 | 5/2014 | Rajagopalan et al. | |
| 8,778,309 | B2 | 7/2014 | Rajagopalan et al. | |
| 9,005,581 | B2 | 4/2015 | Poreddy et al. | |
| 9,114,160 | B2 | 8/2015 | Rajagopalan et al. | |
| 9,283,288 | B2 | 3/2016 | Dorshow et al. | |
| 9,376,399 | B2 | 6/2016 | Rajagopalan et al. | |
| 9,480,687 | B2 | 11/2016 | Rajagopalan et al. | |
| 2003/0236452 | A1 | 12/2003 | Melker et al. | |
| 2006/0095102 | A1 | 5/2006 | Perez | |
| 2008/0281173 | A1 | 11/2008 | Esenaliev et al. | |
| 2011/0230739 | A1 | 9/2011 | Gretz et al. | |
| 2013/0116512 | A1 | 5/2013 | Imran | |
| 2014/0121539 | A1 | 5/2014 | Chatterjee et al. | |
| 2014/0249853 | A1 | 9/2014 | Proud et al. | |
| 2015/0306486 | A1 | 10/2015 | Logan et al. | |
| 2019/0125902 | A1 | 5/2019 | Rajagopalan et al. | |
| 2019/0167167 | A1 | 6/2019 | Mitchell et al. | |
| 2019/0254602 | A1 | 8/2019 | Allen et al. | |
| 2020/0281510 | A1 | 9/2020 | Froehlich et al. | |

FOREIGN PATENT DOCUMENTS

| | | | |
|---|---|---|---|
| WO | 2013064313 | A1 | 5/2013 |
| WO | 2013128329 | A1 | 9/2013 |
| WO | 2014111779 | A1 | 7/2014 |
| WO | 2014195236 | A1 | 12/2014 |
| WO | 2014195438 | A1 | 12/2014 |
| WO | 2014195451 | A1 | 12/2014 |
| WO | 2015104184 | A1 | 7/2015 |
| WO | 2019040849 | A1 | 2/2019 |

OTHER PUBLICATIONS

Chinen et al., "Fluorescence-Enhanced Europium-Diethylenetriaminepentaacetic (DTPA)-Monoamide Complexes for the Assessment of Renal Function," J. Med. Chem., vol. 51, (2008), pp. 957-962.

Dean et al., "Inulin, Diodone, Creatinine And Urea Clearances In Newborn Infants," J. Physiol., vol. 106, (1947), pp. 431-439.

Debreczeny et al., "Transdermal Optical Renal Function Monitoring in Humans: Development, Verification, and Validation of a Prototype Device," Journal of Biomedical Optics, vol. 23, No. 5, (May 2018), pp. 057003-1-057003-9.

Friedman et al., "A comparison of the renal clearances of allantoin and inulin in man," Fed. Proc., vol. 7, No. 1 Pt 1, (1948), 1 page.

Gregory et al., "Studies on Hypertension; Effect of Lowering the Blood Pressures of Hypertensive Patients by High Spinal Anesthesia on the Renal Function as Measured by Inulin and Diodrast Clearances," Arch. Intern. Med. (Chic), vol. 77, (1946), pp. 385-392.

Levin et al., "The Effect of Chronic Anemia on Renal Function as Measured by Inulin and Diodrast Clearances," Proc. Annu. Meet. Cent. Soc. Clin. Res. U. S., vol. 20, (1947), 3 pages.

Nagpal et al., "Combined Fluorescein, Indocyanine angiography and Optical Coherent Tomography Using Spectralis," Rajasthan Journal Of Ophthalmology, (2011), 8 pages.

Navar et al., "Distal Tubular Feedback in the Autoregulation of Single Nephron Glomerular Filtration Rate," J. Clin. Invest., vol. 53, (1974), pp. 516-525.

Nicholson et al., "Renal Function as Affected by Experimental Unilateral Kidney Lesions: I. Nephrosis Due to odium Rartrate," J. Exp. Med., vol. 68, (1938), pp. 439-456.

Pill et al., "Fluorescein-labeled Sinistrin as Marker of Glomerular Filtration Rate," European Journal of Medicinal Chemistry, vol. 40, (2005), pp. 1056-1061.

Poujeol et al., "Glomerular Filtration Rate and Microsphere Distributions in Single Nephron of Rat Kidney," Pflugers Arch., vol. 357, (1975), pp. 291-301.

Robson et al., "The Determination of the Renal Clearance of Inulin in Man," Q. J. Exp. Physiol., vol. 35, (1949), pp. 111-134.

Schock-Kusch et al., "Transcutaneous measurement of glomerular filtration rate using FITC-sinistrin in rats," Nephrol Dial Transplant, vol. 24, (2009), pp. 2997-3001.

Shannon et al., "The Renal Excretion of Inulin and Creatinine by the Anaesthetized Dog and the Pump-Lung-Kidney Preparation", J. Physiol., vol. 98, (1940), pp. 97-108.

Yu et al., "Rapid determination of renal filtration function using an optical ratiometric imaging approach," Am. J. Physiol. Renal. Physiol., vol. 292, (2007), pp F1873-F1880.

International Search Report received for PCT Patent Application No. PCT/US2019/013784, dated May 7, 2019, 3 pages.

International Preliminary Report on Patentability received for PCT Patent Application No. PCT/US2019/013784, dated Jul. 30, 2020, 8 pages.

Acurable; We Create Accurate and User Friendly Wearable Medical Devices Intended to be Used by Patients at Home; product page; 8 pgs; retrieved Sep. 16, 2020 from the Internet: https://acurable.com/.

Apple; Apple Watch Series 5—Technical Specifications; product page; 3 pgs; retrieved Sep. 15, 2020 from the Internet: https://support.apple.com/kb/SP808?viewlocale=en_US&locale=en_US.

Ava; The Ava Bracelet; product page; 5 pgs; retrieved Sep. 16, 2020 from the Internet: https://www.avawomen.com/how-ava-works/healthcare/technology/.

AWAK; AWAK product page; 5 pgs; retrieved Sep. 16, 2020 from the Internet: https://awak.com/product/.

Beddr; Tune your Sleep with the SleepTuner; product page; 20 pgs; retrieved Sep. 16, 2020 from the Internet: https://www.beddrsleep.com/sleeptuner.

Biointellisense; New! BioButton COVID-19 Screening Solution; product page; 12 pgs; retrieved Sep. 16, 2020 from the Internet: https://biointellisense.com/biobutton.

Biovotion; Everion—Revealing Medical Grade Data You Can Act On; 3 pgs; retrieved Sep. 16, 2020 from the Internet: https://www.biovotion.com/everion/.

Dexcom; Dexcom Continuous Glucose Monitoring; product page; 10 pgs; retrieved Sep. 15, 2020 from the Internet: https://www.dexcom.com/g6/features-and-benefits.

Eccrine; Eccrine Systems, Inc. Sweatronics; product page; 4 pgs; retrieved Sep. 16, 2020 from the Internet: https://www.eccrinesystems.com/technology.

Esight; Meet eSight 4; product page; 11 pgs; retrieved Sep. 16, 2020 from the Internet: https://esighteyewear.com/low-vision-device-for-visually-impaired/.

Flextrapower; Smart Insole; product home page. 4 pgs; retrieved Sep. 15, 2020 from the Internet: https://www.flextrapower.com/products/#insole.

Matrix; PowerWatch; product page; 5 pgs; retrieved Sep. 15, 2020 from the Internet: https://www.powerwatch.com/products/powerwatch-2.

Medcomp; products Dignity CT Ports; product page; 1 pg; retrieved Sep. 15, 2020 from the Internet: http://www.medcompnet.com/products/ports/dignity_ct_ports.html.

(56) References Cited

OTHER PUBLICATIONS

Medtronic; InterStim II System; product page; 5 pgs; retrieved Sep. 15, 2020 from the Internet: https://www.medtronic.com/us-en/healthcare-professionals/products/urology/sacral-neuromodulation-systems/interstim-ii.html.
Medtronic; Linq II; product page; 9 pgs; retrieved Sep. 15, 2020 from the Internet: https://www.medtronic.com/us-en/healthcare-professionals/products/cardiac-rhythm/cardiac-monitors/linq-ii.html.
Philips; Biointellisense Biosticker; product page; 8 pgs; retrieved Sep. 16, 2020 from the Internet: https://www.usa.philips.com/healthcare/services/population-health-management/patient-engagement/biointellisense-biosticker.
Proteus; Proteus Digital Health; product page; 4 pgs; retrieved Sep. 16, 2020 from the Internet: https://www.proteus.com/.
Sony; mSafety Technical Specifications; product page; 6 pgs; retrieved Sep. 16, 2020 from the Internet: https://iot.sonynetworkcom.com/msafety/technology.
Vivalink; Fever Scout; product page; 7 pgs; retrieved Sep. 16, 2020 from the Internet: https://www.vivalnk.com/feverscout.
Vivalink; Medical Sensor Platform; product page; 5 pgs; retrieved Sep. 16, 2020 from the Internet: https://www.vivalnk.com/product/platform.
Vivalink; Wellness Quantified Vital Scout; product page; 6 pgs; retrieved Sep. 16, 2020 from the Internet: https://www.vivalnk.com/vitalscout.
Withings; Hybrid Smartwatches; product home page; 13 pgs; retrieved Sep. 16, 2020 from the Internet: https://www.withings.com/us/en/watches.
Zimmer Biomet; mymobility; product page; 9 pgs; retrieved Sep. 15, 2020 from the Internet: https://www.zimmerbiomet.com/medical-professionals/zb-connect/mymobility.html.
Berge et al., "Pharmaceutical Salts", Journal of Pharmaceutical Sciences, Jan. 1977, vol. 66, No. 1, pp. 1-19.
International Search Report for International Application No. PCT/US2019/048319, dated Nov. 20, 2019, 16 pages.

\* cited by examiner

TWO PIECE SENSOR ASSEMBLY AND METHOD OF USE

CROSS REFERENCE TO RELATED APPLICATIONS

This application claims priority benefit of U.S. Provisional Application Ser. No. 62/793,000 filed Jan. 16, 2019, the entire contents of which are incorporated by reference herein.

FIELD OF INVENTION

The field of the disclosure relates generally to sensor systems. More specifically, this disclosure generally relates to a two-piece sensor assembly where the skin sensor that comprises the complex electronic components is reusable and the attachment collar that holds the skin sensor in place on the body of a patient is either disposable or reusable.

BACKGROUND

In the clinical and preclinical field, determining various organ functions is accorded great importance since, for example, corresponding therapies or medications can be controlled in accordance with said organ functions. The two-piece sensor assembly is described hereinafter substantially with regard to kidney function monitoring. In principle, however, other applications are also conceivable in which the function of a particular organ can be detected by means of determining a temporal profile of an indicator substance.

The glomerular filtration rate (GFR) is an important clinical parameter to assess the level of kidney function in a patient. As shown in the table below, the lower the GFR, the more serious the kidney impairment for Chronic Kidney Disease (CKD) and other renal insufficiencies. The GFR can be estimated based on a blood test measuring the blood creatinine level in the patient in combination with other factors. More accurate methods involve the injection of an exogenous substance into a patient followed by careful monitoring of plasma and/or urine concentration over a period of time. These are often contrast agents (CA) that can cause renal problems on their own. Radioisotopes or iodinated aromatic rings are two common categories of CAs that are used for GFR determination.

| Stage | Description | GFR* |
|---|---|---|
| Increased risk | Increase of risk factors (e.g., diabetes, high blood pressure, family history, age, ethnicity) | >90 |
| 1 | Kidney damage with normal kidney function | >90 |
| 2 | Kidney damage with mild loss of kidney function | 60-89 |
| 3a | Mild to moderate loss of kidney function | 44-59 |
| 3b | Moderate to severe loss of kidney function | 30-44 |
| 4 | Severe loss of kidney function | 15-29 |
| 5 | Kidney failure; dialysis required | <15 |

*GFR is measured in units of mL/min/1.73 m$^2$.

With regard to conventional renal function measurement procedures, an approximation of a patient's GFR can be made via a 24 hour urine collection procedure that (as the name suggests) typically requires about 24 hours for urine collection, several more hours for analysis, and a meticulous bedside collection technique. Unfortunately, patient compliance using this method is very low, and, as a consequence, is not generally utilized by clinicians.

Examples of exogenous substances capable of clearing the kidney exclusively via glomerular filtration (hereinafter referred to as "GFR agents") include creatinine, o-iodohippuran, and $^{99m}$Tc-DTPA. Examples of exogenous substances that are capable of undergoing renal clearance via tubular secretion include $^{99m}$Tc-MAG3 and other substances known in the art. $^{99m}$Tc-MAG3 is also widely used to assess renal function though gamma scintigraphy as well as through renal blood flow measurement. One drawback to many indicator substances, such as o-iodohippuran, $^{99m}$Tc-DTPA and $^{99m}$Tc-MAG3, is that they are radioisotopes and therefore require special handling techniques and are associated with risks to patient health.

BRIEF DESCRIPTION

Disclosed here in is a two-piece sensor assembly. The sensor assembly generally comprises: an attachment collar configured to attach to a body surface of a patient and comprising at least one opening, and a skin sensor configured to seat into the at least one opening in the attachment collar. The skin sensor generally comprises: at least one radiation source configured to irradiate the body surface with at least one interrogation light, and at least one detector configured to detect at least one response light incident from the direction of the body surface.

In another aspect, disclosed herein is a method for determining a glomerular filtration rate (GFR) in a patient in need thereof. The method generally comprises: applying a two-piece sensor assembly onto the body surface of the patient, administering into the body of the patient an indicator substance, said indicator substance configured to generate an optical response in response to an interrogation light; detecting said optical response using the two-piece sensor assembly over a predetermined period of time; and determining the GFR in said patient based on the detected optical response.

Figure 1:
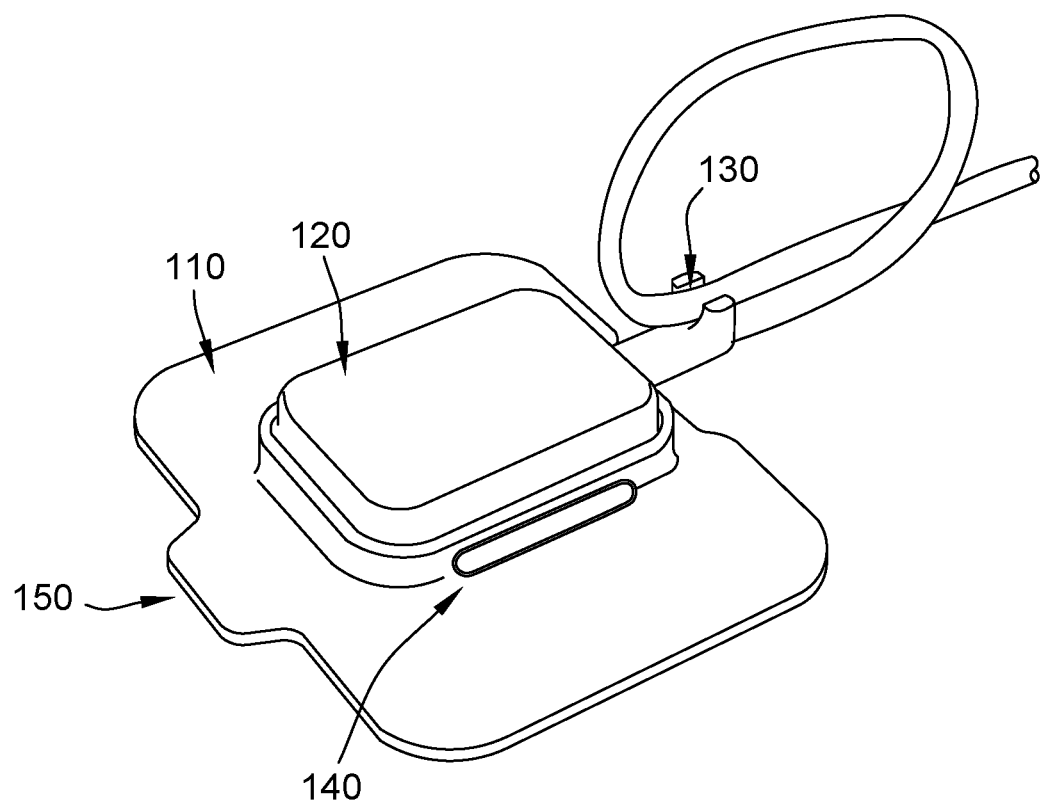
FIG. 1 illustrates one embodiment of the two-piece sensor assembly that includes a locking bar on each side of the sensor to secure it to the attachment collar, a cord management system to provide strain relief and security from cord pulls, and a pull tab for easy removal of the attachment collar from skin.

Unless otherwise indicated, the drawings and figures provided herein illustrate features of embodiments of the disclosure or results of representative experiments illustrating some aspects of the subject matter disclosed herein. These features and/or results are believed to be applicable in a wide variety of systems including one or more embodiments of the disclosure. As such, the drawings are not intended to include all additional features known by those of ordinary skill in the art to be required for the practice of the embodiments, nor are they intended to be limiting as to possible uses of the methods disclosed herein.

DETAILED DESCRIPTION

In the following specification and the claims, reference will be made to a number of terms, which shall be defined to have the following meanings. The singular forms "a," "an," and "the" include plural references unless the context clearly dictates otherwise. The terms "comprising," "including," and "having" are intended to be inclusive and mean that there may be additional elements other than the listed elements. "Optional" or "optionally" means that the subsequently described event or a circumstance may or may not occur, and that the description includes instances where the event occurs and instances where it does not.

Approximating language, as used herein throughout the specification and claims, may be applied to modify any quantitative representation that could permissibly vary without resulting in a change in the basic function to which it is related. Accordingly, a value modified by a term or terms, such as "about," "approximately," and "substantially," are not to be limited to the precise value specified. In at least some instances, the approximating language may correspond to the precision of an instrument for measuring the value. Here and throughout the specification and claims, range limitations may be combined and/or interchanged; such ranges are identified and include all the sub-ranges contained therein unless context or language indicates otherwise.

As used herein, the term "light-tight" means the interface between two surfaces does not permit the passage of external light. For example, when the attachment collar is placed on a body surface and the skin sensor is operably attached to it, a surface of the skin sensor faces the body surface. No external light penetrates to the body surface between the interface of the skin sensor and the attachment collar to reach the area of the body surface that faces the skin sensor. Additionally, no external light passes between the body surface of the patient and the surface or edges of the attachment collar adhered to or in contact with the body surface. As such, the only light detected by the skin sensor emanates directly incident to the body surface of the patient. In some aspects, the only light detected by the skin sensor emanates from a response light generated by an indicator substance inside the body of the patient.

PCT/EP2009/060785, which is incorporated by reference herein in its entirety for all purposes, discloses skin sensors that can, in some aspects, be configured for use in conjunction with an attachment collar thereby creating a two-piece sensor assembly as disclosed herein.

The term "patient" as used herein refers to a warm blooded animal such as a mammal which is the subject of a medical treatment for a medical condition that causes at least one symptom. It is understood that at least humans, dogs, cats, and horses are within the scope of the meaning of the term. In some aspects, the patient is human. As used herein, any suitable surface on the body of the patient may be used as the body surface. Examples include, but are not limited to, skin surfaces, fingernails or toenails, more particularly surfaces exposed to the atmosphere. Generally, as used herein, the term "patient" means a human or an animal on which at least one of the two-piece sensor assembly may be used, independently of the health of the patient.

The skin sensor comprises at least one radiation source. A radiation source is understood to be any device which can emit radiation anywhere on the electromagnetic spectrum. In some aspects, the electromagnetic radiation is in the visible, infrared, ultraviolet, and/or gamma spectral range. Alternatively or additionally, other types of radiation can also be used, for example streams of particles. By way of example and not limitation, alpha rays and/or beta rays may be used. The radiation source is configured to generate radiation of the type mentioned. Without restricting the type of radiation used and for convenience only, hereinafter radiation is generally designated as "light" whether or not it is in the visible region of the electromagnetic spectrum, and the radiation source is described more particularly with reference to a "light source". However, other configurations of the radiation source are possible, in some aspects, and it is also possible, in some aspects, to combine different types of radiation sources.

The radiation source can be, for example, an integral constituent of the skin sensor, for example in the context of a layer construction of the skin sensor. The radiation source is therefore designed to generate at least one interrogation light directly within the skin sensor, in contrast to external generation of the interrogation light. In this respect, the skin sensor differs, for example, from the fiber-optic construction in U.S. Pat. No. 6,995,019 B2, in which an external light source is used. Instead of an individual light source, in some aspects, it is also possible to use a plurality of light sources, for example redundant light sources for emitting one and the same wavelength, and/or a plurality of different light sources for emitting different wavelengths. Generally, the at least one light source is designed to irradiate the body surface with at least one interrogation light.

An interrogation light is understood to be a light that can be used for the detection of an indicator substance as disclosed elsewhere herein, whose light excites the indicator substance inside a body tissue and/or a body fluid of the patient, for example with variable penetration depth, and causing a perceptible response, more particularly, an optically perceptible response. This excitation takes place in such a way that a luminescence, a fluorescence and/or a phosphorescence is initiated in the indicator substance. In some aspects, other types of excitation occur, for example scattering of the light at an identical or shifted wavelength. Generally, at least one response light is generated by the indicator substance in response to the interrogation light.

The interrogation light is designed such that the desired response is excited in a targeted manner in the indicator substance. Accordingly, by way of example and not limitation, a wavelength and/or a wavelength range of the interrogation light and/or some other property of the interrogation light can be adapted or adjusted based on the identity and properties of the indicator substance. This can be done directly by the radiation source, for example, by virtue of the radiation source providing the interrogation light having a specific wavelength and/or in a specified wavelength range and/or by the inclusion of at least one excitation filter being used to filter out the desired interrogation light from a primary light of the light source. In some aspects, the skin sensor performs fluorescence measurements on the indicator substance. Accordingly, the interrogation light can be adapted to the excitation range of the fluorescence of the indicator substance.

The skin sensor further comprises at least one detector designed to detect at least one response light incident from the direction of the body surface. The response light can be light in the sense of the above definition. The detector is also an integral constituent of the skin sensor. The detector is therefore part of the skin sensor such that the response light is detected directly within the skin sensor, in contrast, for example, to the fiber-optic construction in U.S. Pat. No. 6,995,019 B2, in which an external detector is required.

In some aspects, the response light represents an optical response of the indicator substance to the incidence of the interrogation light. Accordingly, the detector and/or the detector in interaction with at least one response filter is configured to detect in a targeted manner in the spectral range of the response light. In some aspects, the detector and/or the detector in interaction with the at least one response filter is configured to suppress light outside the spectral range of the response light. In some aspects, the detector and/or the detector in interaction with the at least one response filter can be designed to suppress the interrogation light. In yet another aspect, response filters are designed to suppress the detection of ambient light, particularly at wavelengths that can travel long distances in tissue prior to absorption, such as a spectral range of from about 700 to about 1100 nm. The interrogation light and the response light can be configured such that they are spectrally different or spectrally shifted relative to one another with regard to their spectral intensity distribution.

By way of example and not limitation, in some aspects, the response light shifts toward longer wavelengths in comparison with the interrogation light, which generally occurs in a fluorescence measurement (i.e., the Stokes shift). By way of another example, the Stokes shift of a peak wavelength of the response light relative to a peak wavelength of the interrogation light is between about 10 nm and about 200 nm, more particularly between about 100 nm and about 150 nm, and particularly about 120 nm. The detector and/or the detector in interaction with the at least one response filter can be designed to detect such response light. About in this context means±10 nm.

The at least one radiation source, more particularly, the at least one light source, and the at least one detector are designed to irradiate the body surface with the interrogation light and to detect at least one response light incident from the direction of the body surface. The radiation source and the detector are therefore optically connected to the body surface in such a way that, through the body surface, for example transcutaneously, the interrogation light can be radiated into the body tissue or the body fluid of the patient, and that, likewise through the body surface, for example transcutaneously, the response light from the body tissue or the body fluid is observed by the detector.

In addition to the at least one detector and the at least one radiation source, the sensor assembly may comprise further elements. In some aspects, the attachment collar comprises further elements. In some aspects, the skin sensor comprises further elements. In some aspects, both the skin sensor and the attachment collar comprise further elements. Thus, the skin sensor can comprise, for example, at least one interface for data exchange. Said data can be, for example, measurement results for intensities of the response light detected by the detector. Data already partly processed, filtered or partly or completely evaluated data, can also be transmitted via said interface. The interface can be configured as a wireless interface, a cabled interface or a combination thereof, and can comprise a radiofrequency coil and/or a cable. In some aspects, transponder technology known in the art may be used, for example, to initiate a measurement via the skin sensor and/or to interrogate measurement data from the skin sensor. In some aspects, corresponding radiofrequency readers such as are known from RFID technology (radiofrequency identification label technology), for example, can be used for this purpose.

In some aspects, the two-piece sensor assembly further comprises a controller. The controller is programmed to control the at least one skin sensor comprising the at least one radiation source and the at least one detector. In some aspects, the controller is further programmed to receive authentication information from the skin sensor, the attachment collar or both. The authentication information can be using techniques known in the art such as, for example, EPROM or RFID. In some aspects, the connection between the controller and the skin sensor is cabled, wireless or a combination thereof. In some aspects, the connection between the controller and the other components is by a cable. In some aspects, the connection between the controller and the other components is wireless. In some aspects, the controller is contained within the sensor.

Furthermore, the sensor assembly can comprise at least one driving or controlling electronic unit. Said driving electronic or controlling unit can be configured, for example, for driving or controlling the at least one radiation source and the at least one detector, for example, for starting an emission of the interrogation light and/or for initiating a detection of the response light. For this purpose, the driving or controlling electronic unit can comprise, for example, corresponding drivers for the detector and/or the radiation source. A timing for a measurement can also be predefined, such that, for example, the driving or controlling electronic unit can predefine a specific time scheme for the light source and/or the detector, said time scheme allowing a temporal sequence of the emission of the interrogation light and the detection of the response light. By way of example and not limitation, the driving electronic unit can be designed to carry out or to control a temporally resolved measurement of the skin sensor. In this case, a measurement comprises the emissions of at least one interrogation light, more particularly of at least one pulse of the interrogation light, and the detection of at least one response light, more particularly of at least one pulse of the response light. A temporally resolved measurement can accordingly be understood to be a measurement in which, in addition, a time of the detection of the response light also plays a part or is registered. Thus, by way of example and not limitation, for each value of the response light, it is also possible to register the corresponding points in time at which this value is recorded and/or it is possible for the response light only to be recorded at specific points in time (gating). In this way, by means of temporally resolved measurements, for example, it is possible to obtain information about the rate in which an indicator substance is eliminated from the body of a patient via the kidneys. In some aspects, the detector is configured to detect the different time points generated by the interaction of an indicator substance with a light generated by the light source. In some aspects, the controller and the driving or controlling electronic unit are the same device. In some aspects, the driving and controlling electronic unit is an integrated component in the controller. In some aspects, the light source is modulated rather than pulsed, and the detected signal is selectively amplified or digitally demodulated to selectively detect signals at the frequency of the source.

In some aspects, the two-piece sensor assembly further comprises a cable management system configured to reduce or eliminate accidental cord pulls that would dislodge or detach the two-piece sensor assembly from the body of the patient and/or reduce or eliminate accidental cord pulls that would dislodge or detach the skin sensor from the attachment collar, said cable management system is attached to the attachment collar, the skin sensor or both.

In order to reduce possible light transmission through the skin sensor and the attachment collar, in some aspects, one or both are fabricated out of elastomeric materials. In some aspects, the elastomer is mixed with graphite and/or carbon black and/or other light-absorbing materials. In some aspects, an optically non-transmissive material is included as a layer. In some aspects, the optically non-transmissive material is mylar. Mylar is highly absorptive of UV, visible and near infrared light while also being thin and flexible. In another aspect, the optically non-transmissive material is aluminum. Aluminum is also highly absorptive of UV, visible and near infrared light while also being thin and flexible. This reduces light transmission through the skin sensor and/or attachment collar. In some aspects, both the skin sensor and the attachment collar are fabricated from an elastomer that is mixed with graphite, carbon black or a combination thereof. A optically non-transmissive material is one that reduces or eliminates the passage of light therethrough. In some aspects, the passage of light is entirely eliminated. In some aspects, the passage of light is reduced by about 99%, by about 98%, by about 97%, by about 96%, by about 95%, or by about 90%. About as used in this context means±1%. In some aspects, the attachment collar is disposable.

In some aspects, the skin sensor and attachment collar are designed to ameliorate the effects of accumulation of excess fluid within the skin of the patient beneath the sensor, which could otherwise have detrimental or undesirable effects on the sensor measurements. In some aspects, where the rate of elimination of an exogenous agent is being measured, variation over time in the fractional volume of interstitial fluid within the measured tissue volume may result in uncertainty and/or inaccuracy in the transdermally measured elimination rate. Such may be the case when the sensor is placed over an area that is locally edematous, or in patients with whole-body excess fluid build-up ("fluid over-load") such as is common in patients with, for example, compromised kidney function or congestive heart failure. Such excess fluid may be removed from the field of measurement by the application of light pressure against the skin (e.g., 10-20 mm Hg), without exsanguinating the skin or shifting the balance of more tightly bound interstitial fluid. In some aspects, a positive pressure is exerted on the surface of the skin directly beneath the skin sensor, while simultaneously applying a negative pressure on the surrounding skin surface, beneath which the attachment collar is mounted. In some aspects, this is accomplished by first securely mounting the attachment collar to the skin, then mounting the skin sensor into the collar such that the sensor protrudes slightly beyond the collar, thereby pressing more firmly against the skin beneath the sensor, with a compensating negative pressure in the area beneath the attachment collar.

In some aspects, a 2-sided adhesive is employed within an aperture inside the attachment collar. The side facing the skin is selected to adhere reliably to the skin for an extended period of time (e.g., 24 to 48 hrs.), even in the presence of moisture, such as sweat. In some aspects, an acrylate-based adhesive is used for bonding to the skin. In yet another aspect, the skin is pre-treated with a barrier film, such as by application of rapidly-drying liquid film that upon drying forms a "second skin". In such aspects the barrier film aids in the long-term, reliable attachment of the acrylate-based adhesive to the skin, while also having the benefit of allowing sensor removal without disruption or removal of the skin epidermis. In some aspects, the barrier film is CAVILON™ (manufactured by 3M). The second side of the adhesive, which faces towards the sensor, may be selected to adhere as strongly as desired to the face of the sensor. In one such aspect the sensor face is constructed from a polymer material, such as MAKROLON™, and the adhesive is rubber based. One non-limiting example of an appropriate 2-sided adhesive is 3M product #2477 (Double-Coated TPE Silicone Acrylate Medical Tape with Premium Liner).

In some aspects, the adhesive bond formed between the attachment collar and sensor is relatively weak or even non-existent until the adhesive is placed under mild pressure. Such embodiments have the additional benefit of forming a secure interface between the sensor and the skin when the sensor is placed under positive pressure against the skin, but once released, the sensor is easily removed from the attachment collar without leaving a residue on the sensor. In some aspects where the sensor is reusable and the collar is disposable or single use, the sensor portion never contacts the skin. If the sensor does not come into direct contact with the skin of the patient, this reduces the chance of contamination and reduces the cleaning and/or sterilization needed before the sensor is reused on the same or a different patient.

The above-described advantages for the sensor that applies a small positive pressure over the skin area under measurement may be combined with the also above-described aspect wherein a small positive pressure is required to adhere the sensor to the attachment collar. A nonlimiting example that illustrates these advantages is shown in in FIG. 17. These same advantages and features may also be incorporated into other embodiments illustrated herein.

In some aspects, it is desirable that a method for reliably or securely identifying or authenticating the attachment collar is provided. In some aspects the collar includes an encrypted identifier or identification tag that prevents the use on non-approved devices. In some aspects the encryption code is embedded in an EEPROM chip within the attachment collar. Use of the sensor is prevented unless a connection is made between the sensor and collar, and the collar is identified as being valid. In other aspects, the EEPROM is used to identify a particular product version, mode of operation, and/or algorithm coefficients for instrument operation. In this manner, different functions of the sensor may be enabled through the EEPROM coding.

In some aspects, the attachment collar further comprises a pressure sensitive element that communicates with the sensor when attached. In some aspects, the pressure sensor provides an indication of secure attachment of the skin sensor to the skin of the patient. In some aspects, the indication that the sensor is no longer securely attached is used to discontinue measurement, and/or to provide feedback to a user.

In some aspects, the attachment collar is intended for single use and the pressure sensor is used to enforce this. In some aspects, the pressure sensor determines that the attachment collar has been placed on a patient, and then determines that it has been subsequently removed. Any subsequent attempts to reuse the sensor with the same attachment collar are prevented.

With reference to FIG. 1, the two-piece sensor comprises an attachments collar 110 and a sensor 120. The cable is clipped into a cable management system 130 to reduce cord pulls and provide strain relief. Sidebars 140 secure sensor 120 to attachment collar 110, while pull tab 150 allows for easy removal of attachment collar 110 from the skin of the patient after use.

Figure 2:
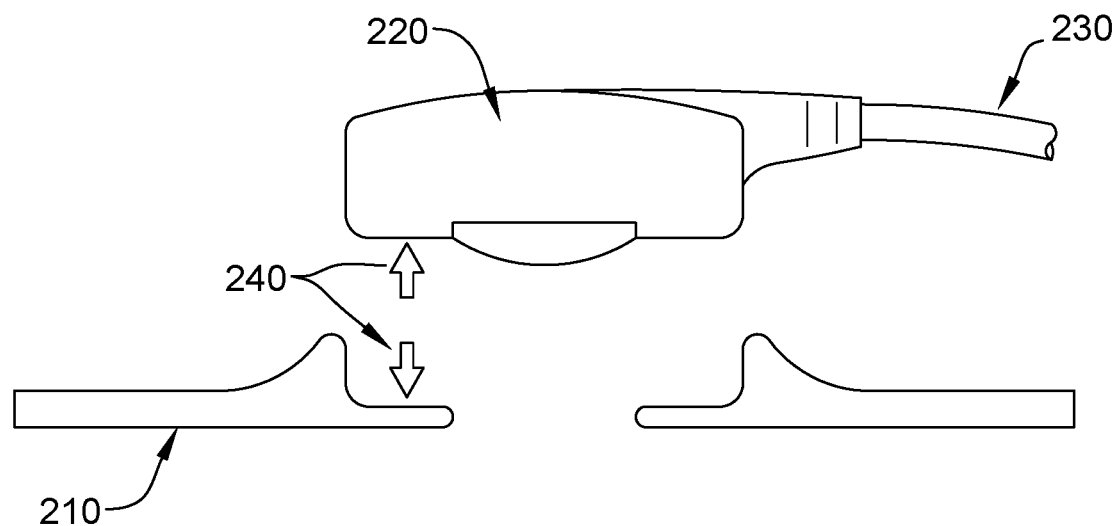
FIG. 2 illustrates one embodiment of the two-piece sensor assembly for attaching the skin sensor to the attachment collar using selectively adhesive surfaces.

With reference to FIG. 2, the two-piece sensor comprises an attachment collar 210 and a sensor 220. Cable 230 is coupled to a controller that can send and receive information therebetween. Also shown and represented by the arrows is a selective adhesive 240 that secures sensor 220 to attachment collar 210.

Figure 3:
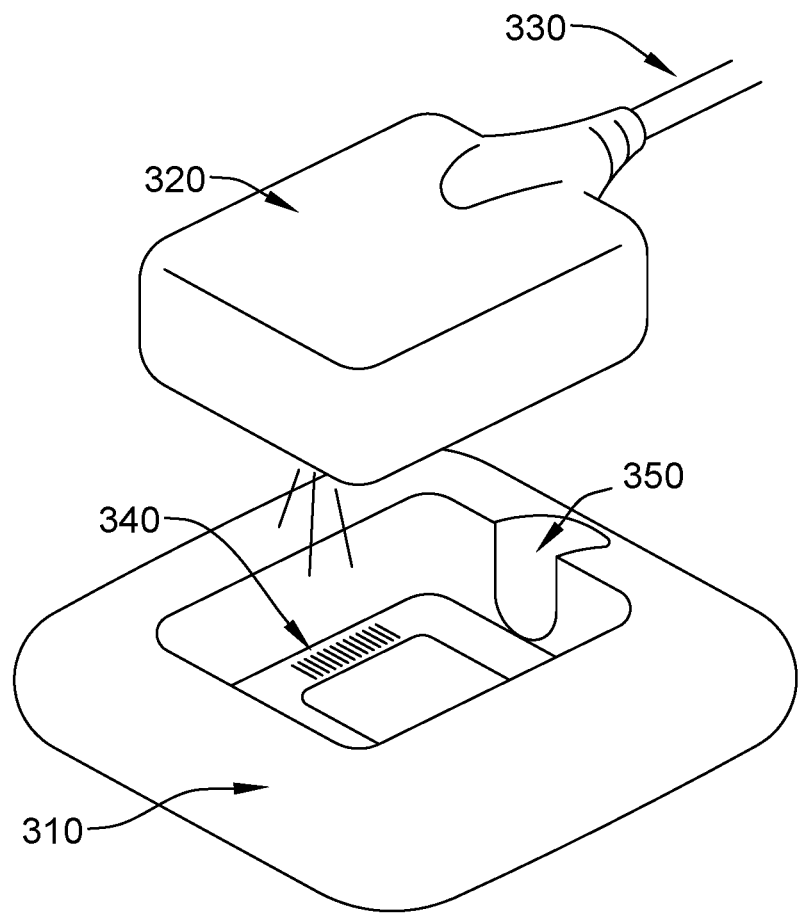
FIG. 3 illustrates one embodiment of the two-piece sensor that includes a bar code/QR reader.

With reference to FIG. 3, the two-piece sensor comprises an attachment collar 310 and a sensor 320. Cable 330 is coupled to a controller that can send and receive information therebetween. Also shown is a bar code 340 that is used to authenticate the combination of sensor 320 and attachment collar 310 thereby ensuring that a light-tight fit and secure attachment to the patient's body surface is achieved. Also shown is cable management groove 350 to help reduce the opportunity for the cable to become caught and dislodged from the patient.

Figure 4:
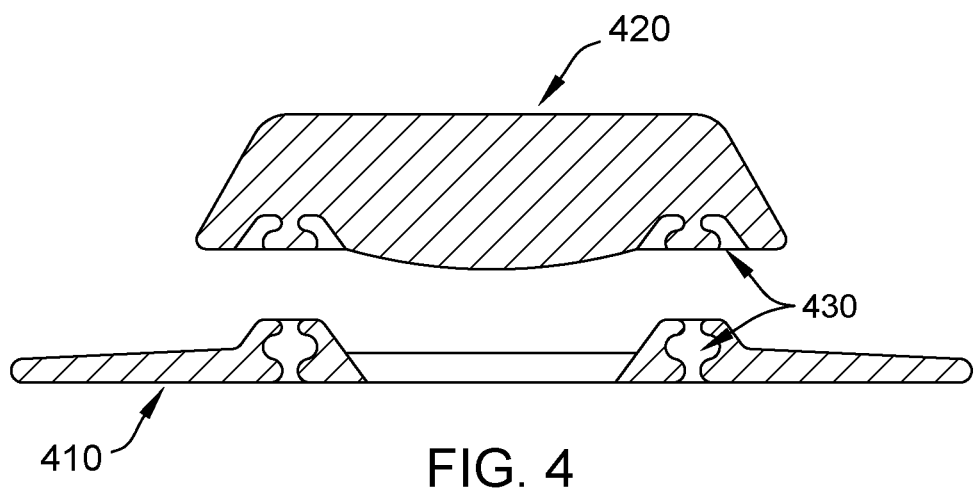
FIG. 4 illustrates a torturous light path for the connection between the skin sensor and the attachment collar to ensure a light-tight fit.

With reference to FIG. 4, the two-piece sensor comprises an attachment collar 410 and a sensor 420. Also shown is one possible aspect of a light-tight connector 430 between sensor 420 and attachment collar 410. The non-linear surfaces of light-tight connector 430 reduces and/or eliminates extraneous light that may leak through between the interface of sensor 420 and attachment collar 410.

Figure 5:
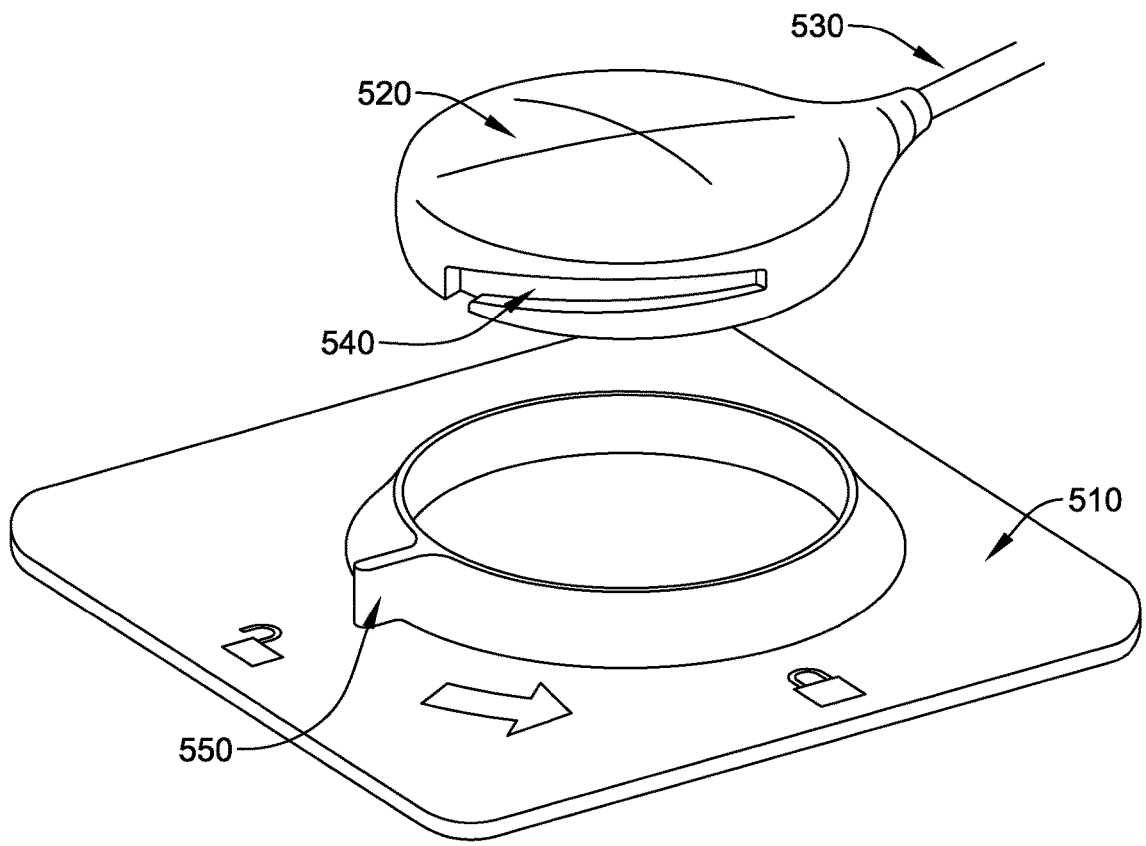
FIG. 5 illustrates a cam lock between the skin sensor and the attachment collar.

With reference to FIG. 5, the two-piece sensor comprises an attachment collar 510 and a sensor 520. Also shown is one possible cam locking mechanism 530 that would secure sensor 520 to attachment collar 510. Sensor 520 would slidably connect tab 550 to slot 540 and then twist to secure the sensor in place ensuring that a secure attachment to the patient's body surface is achieved. This locking mechanism would also be light-tight due to the nonlinear aspect of the male and female ends of the lock.

Figure 6:
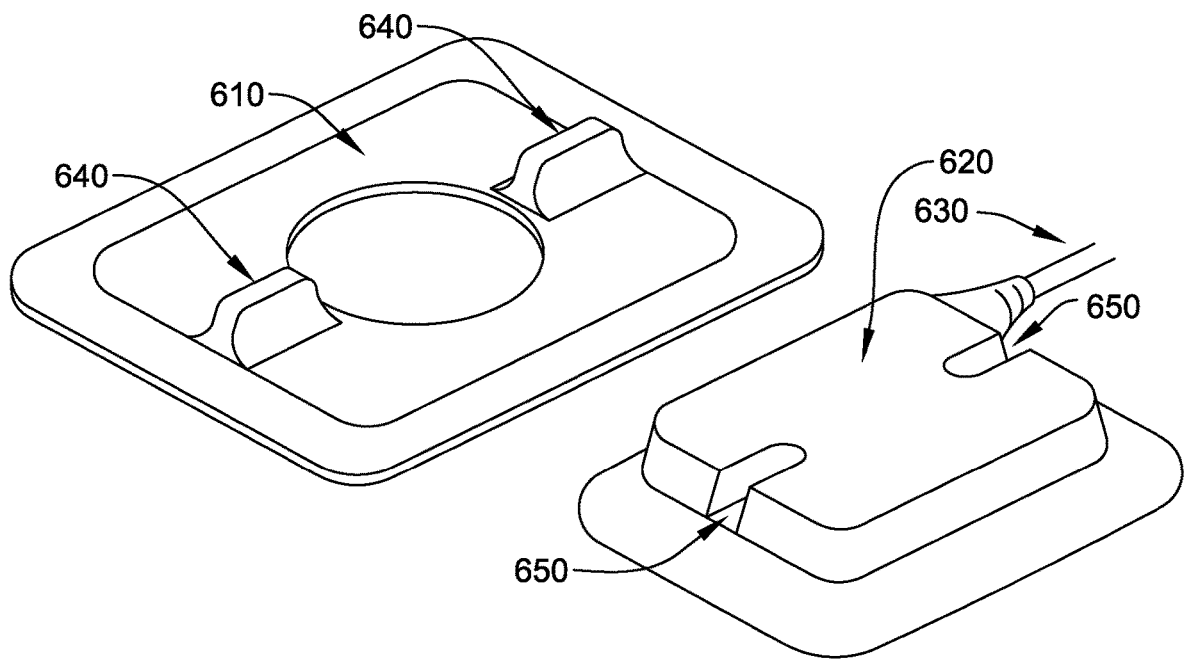
FIG. 6 illustrates one embodiment of the two-piece sensor assembly that comprises tabs to aid the alignment and positioning of the skin sensor relative to the attachment collar.

With reference to FIG. 6, the two-piece sensor comprises an attachment collar 610 and a sensor 620. Cable 630 is coupled to a controller that can send and receive information therebetween. In this aspect, tabs 640 fit into slots 650 thereby ensuring proper alignment of sensor 620 with attachment collar 610 ensuring that a secure attachment and light-tight fit to the patient's body is achieved.

Figure 7:
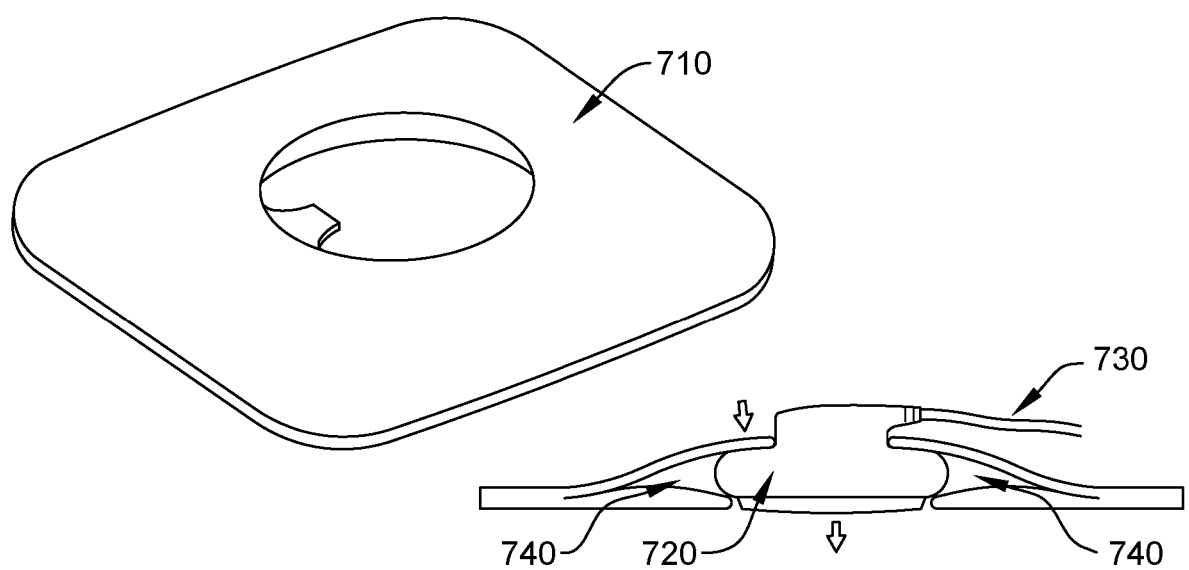
FIG. 7 illustrates a stretch pocket attachment collar for the two-piece sensor assembly that provides a slight downward pressure to the skin sensor onto the skin of the patient.

With reference to FIG. 7, the two-piece sensor comprises an attachment collar 710 and a sensor 720. Cable 730 is coupled to a controller that can send and receive information therebetween. In this aspect, attachment collar 710 is a stretchable pocket that includes an internal cavity 740 therein that receives sensor 720 ensuring a light-tight fit.

Figure 8:
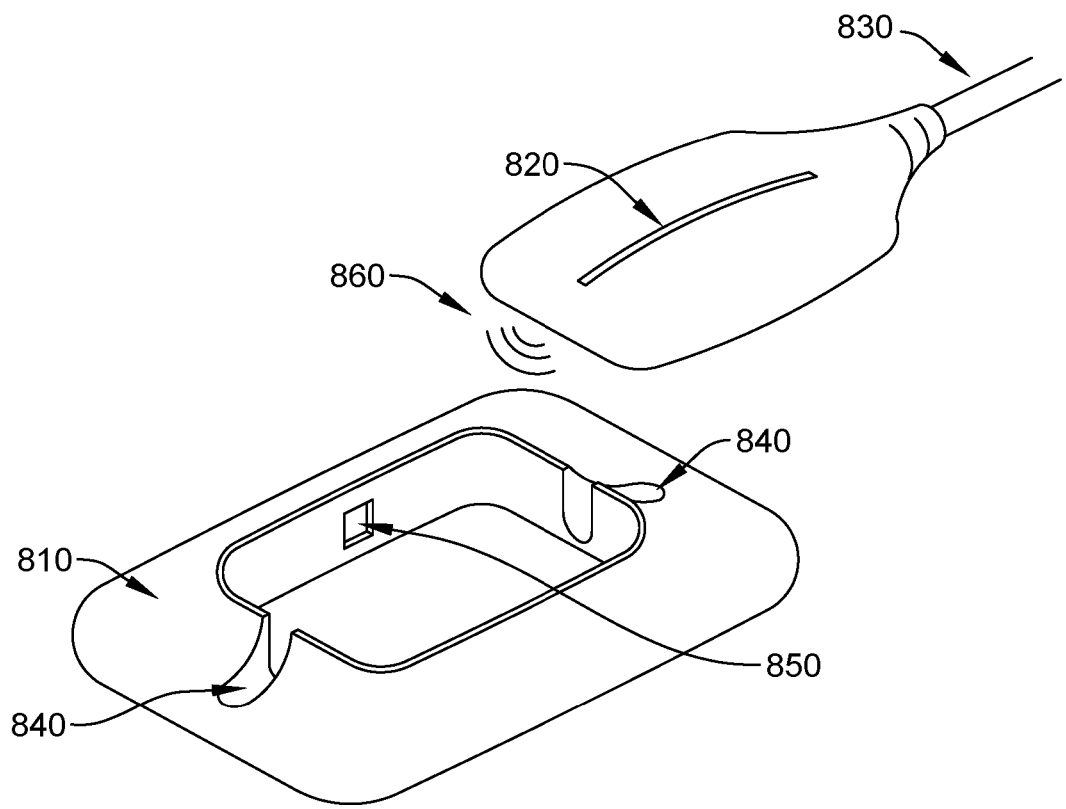
FIG. 8 illustrates one embodiment of the two-piece sensor assembly that includes RFID authentication and grooves within the attachment collar for the cord to provide security from cord pulls.

With reference to FIG. 8, the two-piece sensor comprises an attachment collar 810 and a sensor 820. Cable 830 is coupled to a controller that can send and receive information therebetween. In this aspect, slot 840 could receive and secure cable 830 thereby reducing the incidence of cord-pull by the patient. Also shown is an RFID chip 850 that includes a security code that must be detected 860 by the sensor in order for the system to operate. This RFID code can be used for device security, for ensuring that a secure attachment and light-tight fit to the patient's body is achieved, and for inventory control.

Figure 9:
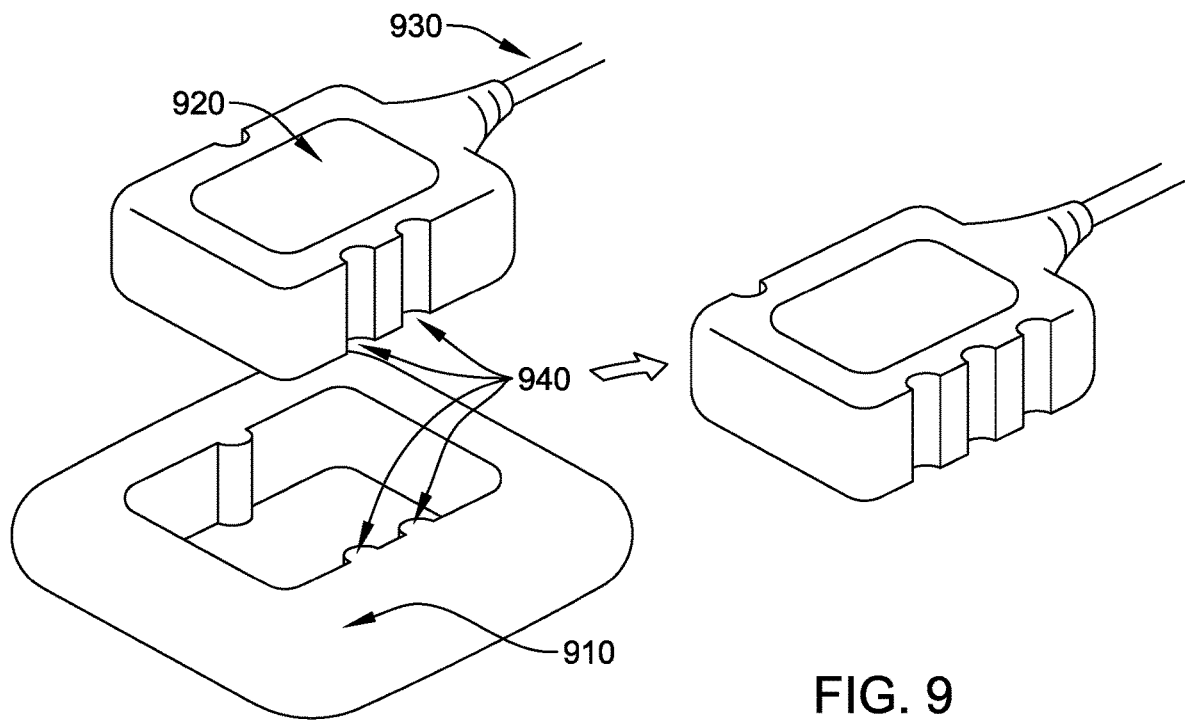
FIG. 9 illustrates one embodiment of the two-piece sensor assembly that includes a lock and key type security feature between the attachment collar and the skin sensor.

With reference to FIG. 9, the two-piece sensor comprises an attachment collar 910 and a sensor 920. Cable 930 is coupled to a controller that can send and receive information therebetween. In this aspect, slots 940 are present to ensure a proper connection between sensor 920 and attachment collar 910. The shape of the slots can be varied in the manner of a lock and key to ensure a secure attachment and as a form of fraud prevention and quality control.

Figure 10:
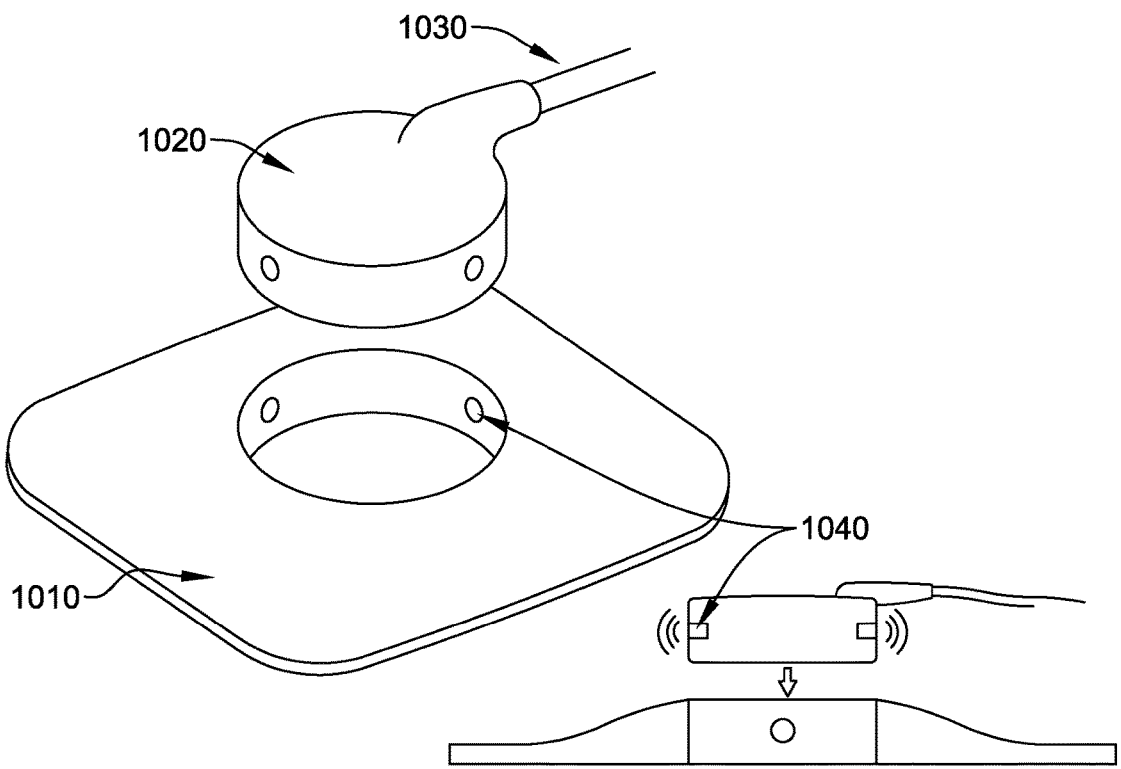
FIG. 10 illustrates one embodiment of the two-piece sensor assembly that includes a magnetic connection between the attachment collar and the skin sensor.

With reference to FIG. 10, the two-piece sensor comprises an attachment collar 1010 and a sensor 1020. Cable 1030 is coupled to a controller that can send and receive information therebetween. In this aspect, magnets 1040 are present to secure sensor 1020 to attachment collar 1010.

Figure 11:
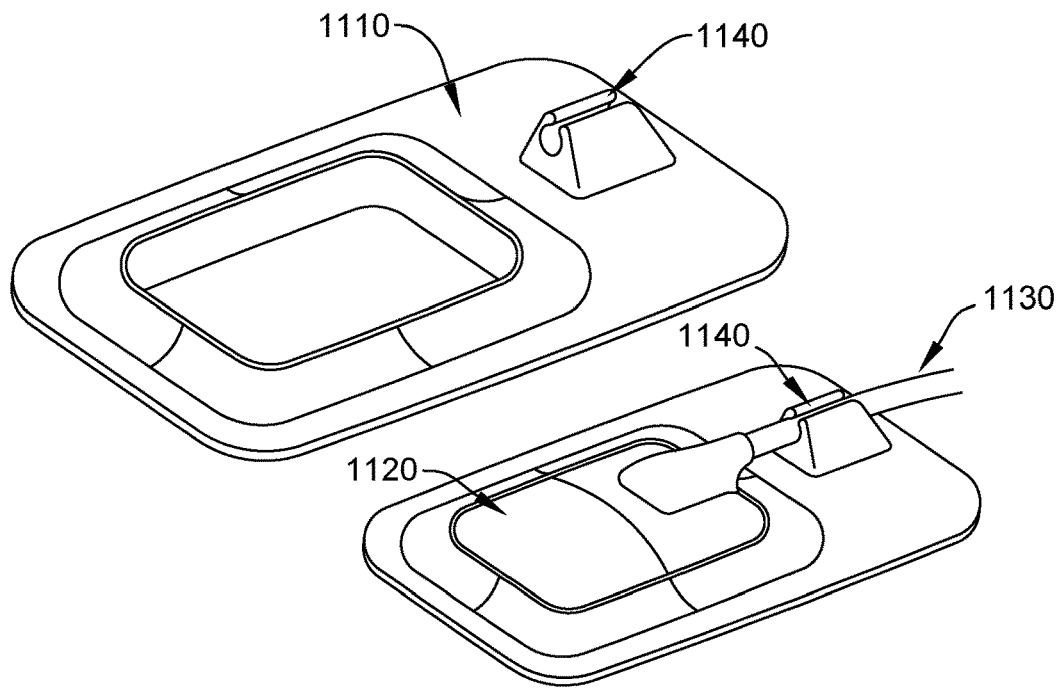
FIG. 11 illustrates one embodiment of the two-piece sensor assembly that includes an attachment collar that encircles the sensor, and a cable management system to provide strain relief and security from cord pulls.

With reference to FIG. 11, the two-piece sensor comprises an attachment collar 1110 and a sensor 1120. Cable 1130 is coupled to a controller that can send and receive information therebetween. In this aspect, cable clip 1140 is on attachment collar 1110 to secure cable 1130 to reduce or eliminate the incidence of cord-pull that would interfere with the use of the system.

Figure 12:
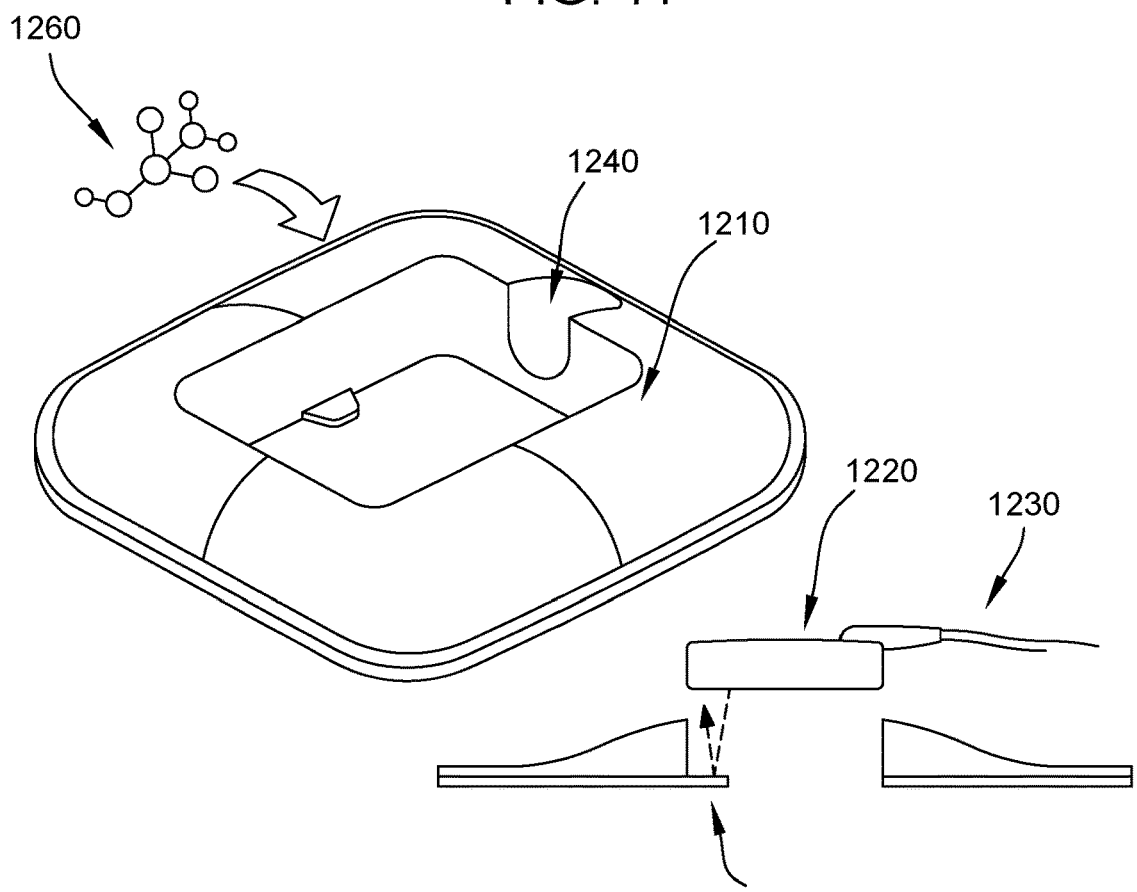
FIG. 12 illustrates one embodiment of the two-piece sensor assembly that includes an embedded chemical in the attachment collar that can be detected by the sensor.

With reference to FIG. 12, the two-piece sensor comprises an attachment collar 1210 and a sensor 1220. Attachment collar 1210 comprises an embedded chemical 1260 that is detected by sensor 1220 when properly placed to provide a secure connection. Cord 1230 seats into slot 1240 thereby reducing movement and play in the cord. Also included is identifier tab 1250 that is used to authenticate the attachment collar 1210 after detection by sensor 1220.

Figure 13:
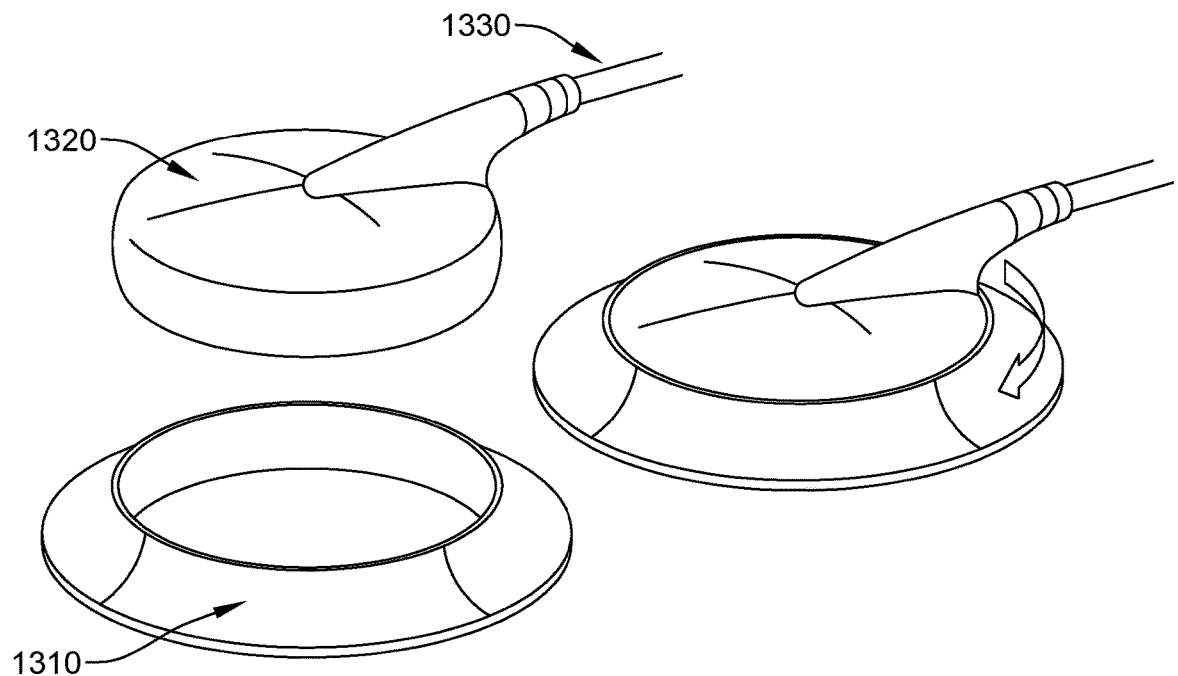
FIG. 13 illustrates one embodiment of the two-piece sensor assembly that includes a swivel attachment between the skin sensor and the attachment collar.

With reference to FIG. 13, the two-piece sensor comprises an attachment collar 1310 and a sensor 1320. Cable 1330 is coupled to a controller that can send and receive information therebetween. In this aspect, sensor 1320 screws into attachment collar 1310 to provide a secure connection and light-tight interface between them.

Figure 14:
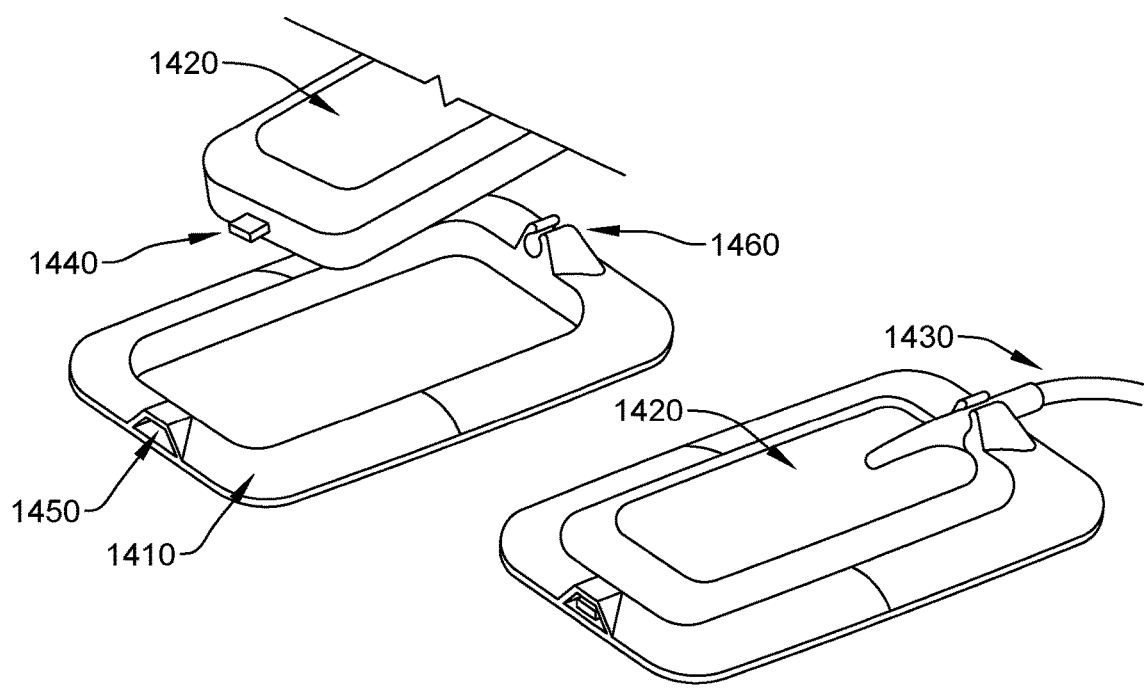
FIG. 14 illustrates one embodiment of the two-piece sensor assembly that includes a tab placement port and cord management system to provide strain relief and security from cord pulls.

With reference to FIG. 14, the two-piece sensor comprises an attachment collar 1410 and a sensor 1420. Cable 1430 is coupled to a controller that can send and receive information therebetween. In this aspect, tab 1440 fits into slot 1450 to secure sensor 1420 to attachment collar 1410. Cable 1430 fits into cable clip 1460 to secure the cable and reduce or eliminate the incidence of cord-pull that would interfere with the use of the system.

Figure 15:
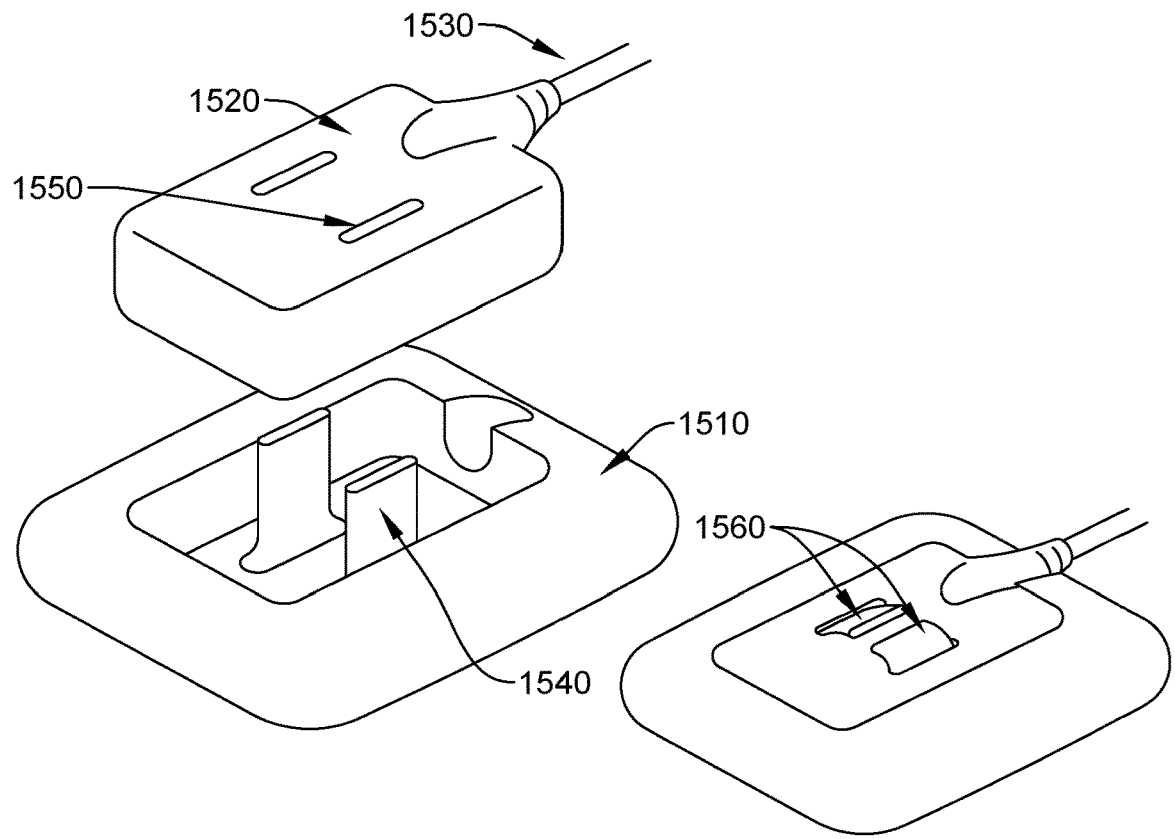
FIG. 15 illustrates one embodiment of the two-piece sensor assembly that includes fold-over tabs to secure the skin sensor to the attachment collar.

With reference to FIG. 15, the two-piece sensor comprises an attachment collar 1510 and a sensor 1520. Cable 1530 is coupled to a controller that can send and receive information therebetween. In this aspect, tabs 1540 fit through slots 1550 on sensor 1520 and fold over 1560 to secure sensor 1520 to attachment collar 1510 ensuring that a secure attachment and light-tight fit to the patient's body is achieved.

Figure 16:
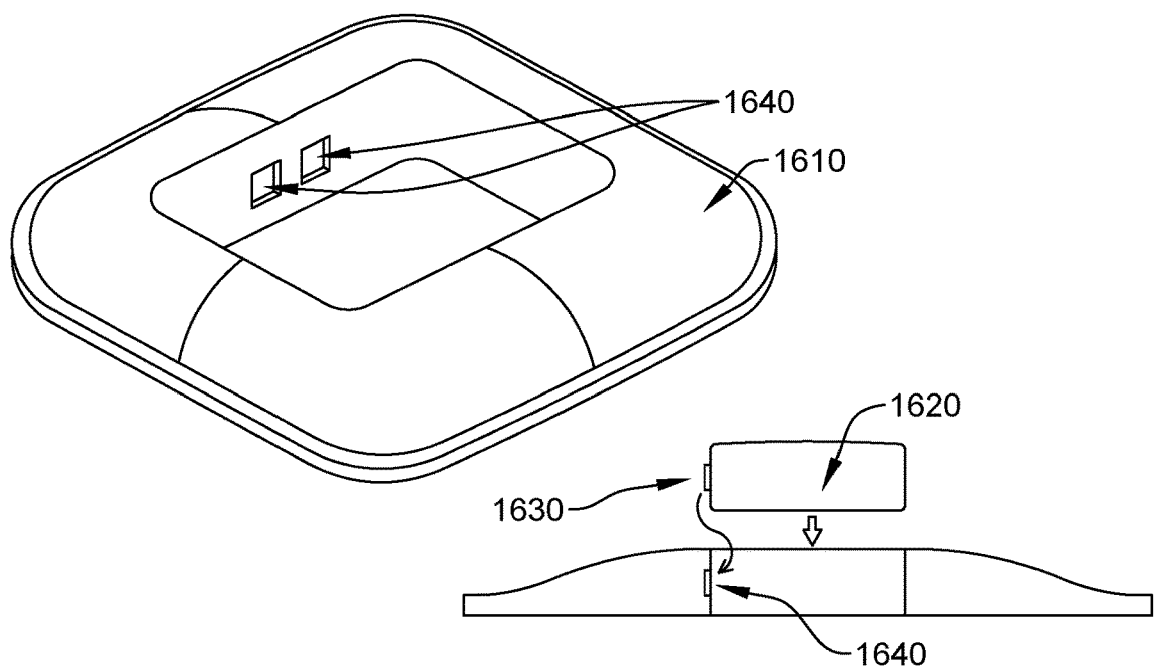
FIG. 16 illustrates one embodiment of the two-piece sensor assembly that includes a communication port (e.g., an EEPROM) between the skin sensor and the attachment collar.

With reference to FIG. 16, the two-piece sensor comprises an attachment collar 1610 and a sensor 1620. The cable (not shown) is coupled to a controller that can send and receive information therebetween. In this aspect, tabs 1630 would insert into holes 1640 thereby ensuring a secure connection between sensor 1620 and attachment collar 1610. Holes 1640 could also be communication ports to send and receive information between sensor 1620 and attachment collar 1610 for both security and inventory purposes. This would eliminate the need for a wireless authentication thereby reducing the complexity and electronic components required in the overall system. In some aspects, communication between sensor 1620 and attachment collar 1610 is via an EPROM type memory ensuring that a secure attachment and light-tight fit to the patient's body is achieved.

Figure 17:
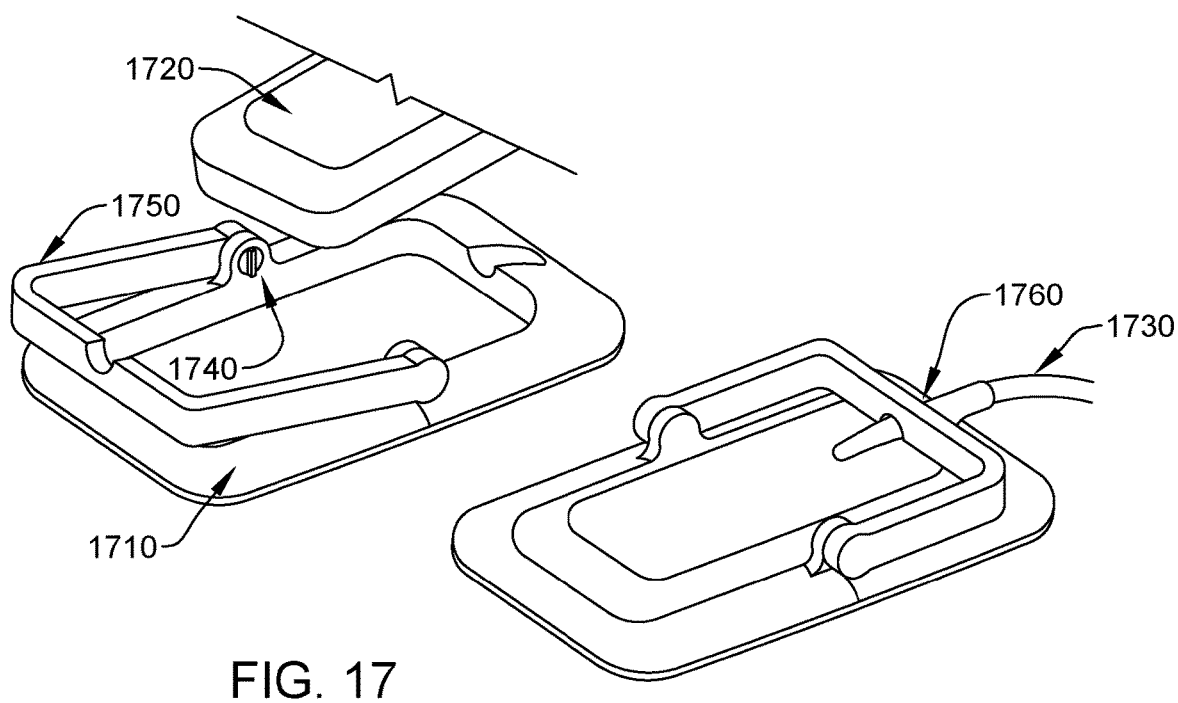
FIG. 17 illustrates one embodiment of the two-piece sensor assembly that includes a cam lock to secure the skin sensor to the attachment collar, and providing a slight downward pressure to the skin sensor onto the skin of the patient and visual indication that the sensor is locked in place.

With reference to FIG. 17, the two-piece sensor comprises an attachment collar 1710 and a sensor 1720. Cable 1730 is coupled to a controller that can send and receive information therebetween. In this aspect, a cam-lock 1740 secures sensor 1720 to attachment collar 1710 after engaging locking arm 1750. Simultaneously, when locking arm 1750 is engaged to secure sensor 1720, it also secures cable 1730 in a secure configuration 1760 ensuring that a secure attachment and light-tight fit to the patient's body is achieved.

Figure 18:
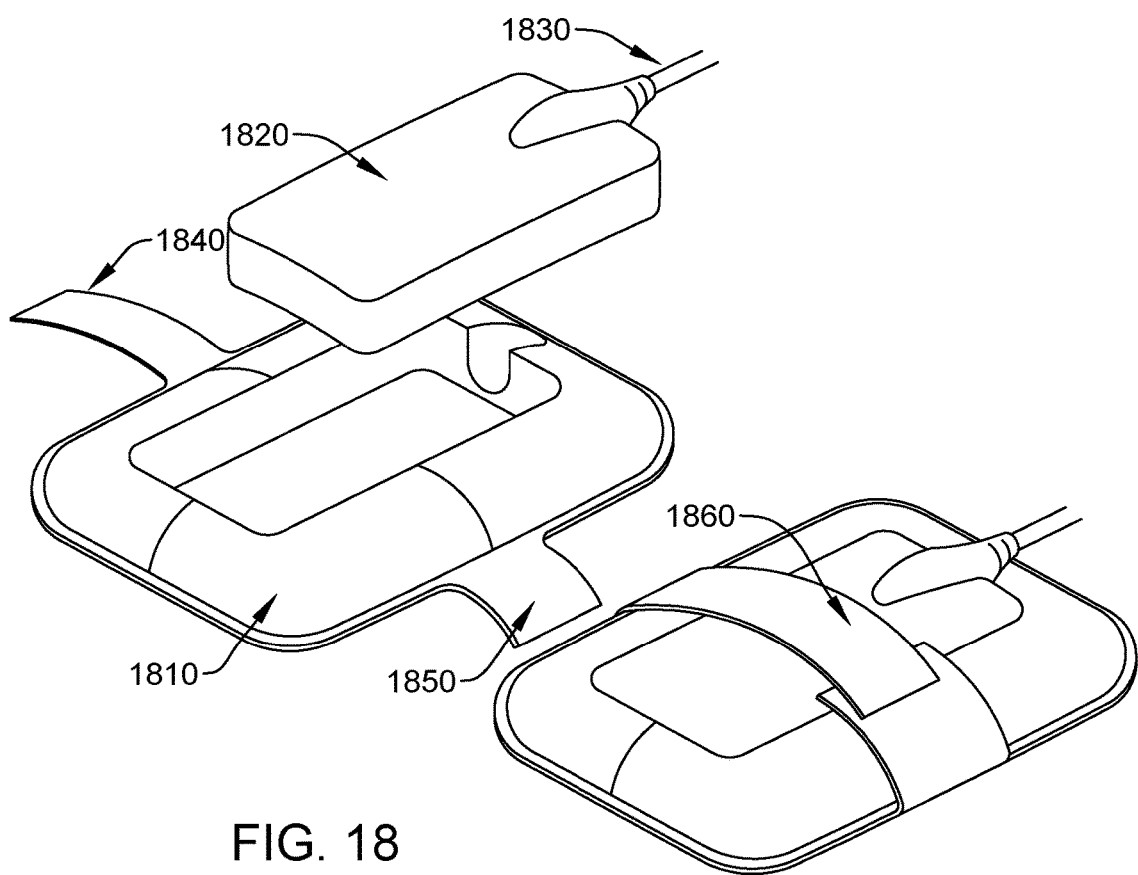
FIG. 18 illustrates one embodiment of the two-piece sensor assembly that includes a wrap mechanism to secure the skin sensor to the attachment collar, and providing a slight downward pressure to ensure a light-tight fit.

With reference to FIG. 18, the two-piece sensor comprises an attachment collar 1810 and a sensor 1820. Cable 1830 is coupled to a controller that can send and receive information therebetween. Sensor 1820 is securely attached to attachment color 1810 via a strap 1840 that engages with tab 1850.

Engagement 1860, in some aspects, can be using Velcro, an adhesive, snap, buckle or other appropriate means ensuring that a secure attachment and light-tight fit to the patient's body is achieved.

Figure 19:
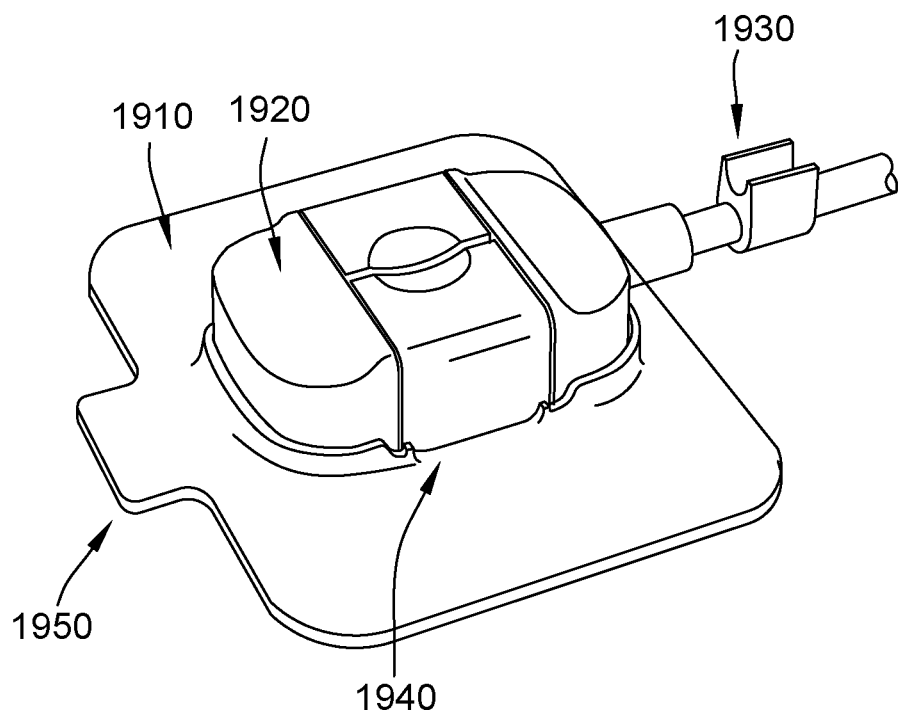
FIG. 19 illustrates one embodiment of the two-piece sensor assembly that includes clips on the skin sensor which secure the sensor to the attachment collar, a cord management system to provide strain relief and security from cord pulls, and a pull tab for easy removal of the attachment collar from the skin when the session is complete.

With reference to FIG. 19, the two-piece sensor comprises an attachment collar 1910 and a sensor 1920. The cable includes a cable management clip 1930 to secure the cord and reduce cord pulls and provide strain relief. Side clips 1940 secure sensor 1920 to attachment collar 1910 while pull tab 1950 allows for easy removal from the skin of a patient after use.

Figure 20:
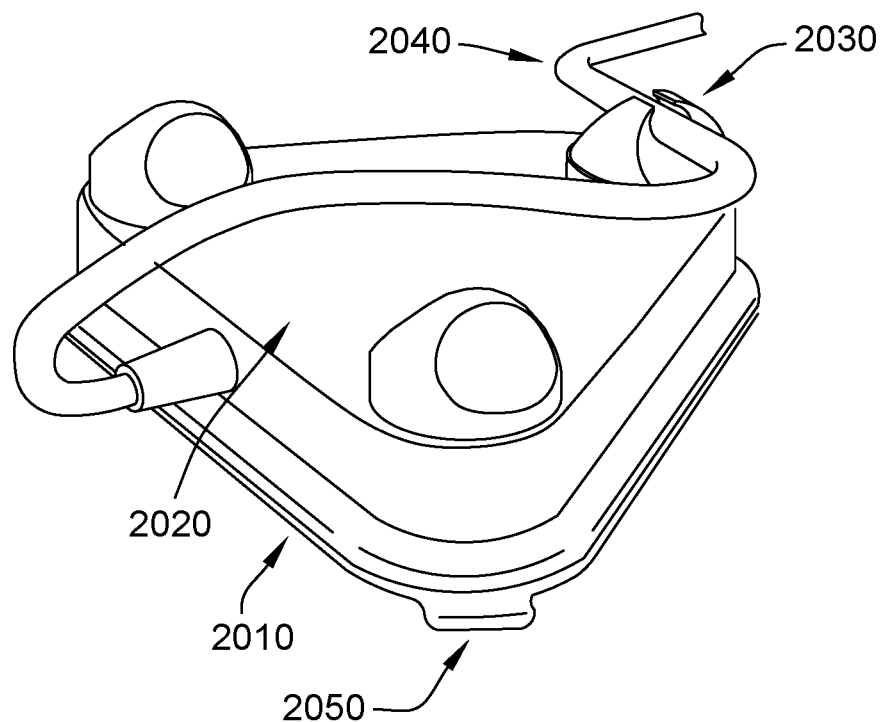
FIG. 20 illustrates one embodiment of the two-piece sensor assembly that includes a locking mechanism on the skin sensor which secures the sensor to the attachment collar, a cord management system to provide strain relief and security from cord pulls, and a pull tab for easy removal of the attachment collar from the skin when the session is complete.

With reference to FIG. 20, the triangular shaped two-piece sensor comprises an attachment collar 2010 and a sensor 2020. Cable 2040 clips into cable management system 2030 to reduce cord pulls and provide strain relief. Pull table 2050 allows for easy removal from the skin of a patient after use.

Figure 21:
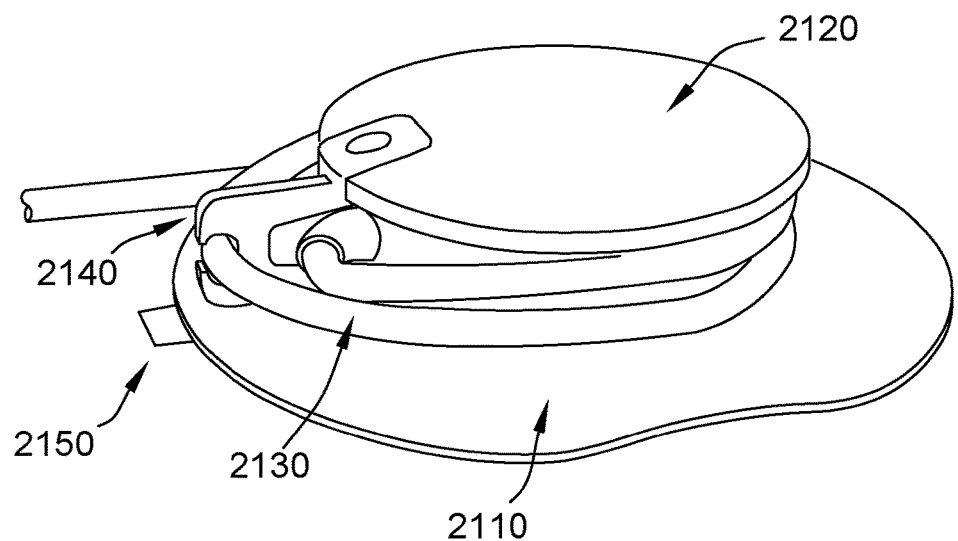
FIG. 21 illustrates one embodiment of the two-piece sensor assembly that includes an attachment collar that encircles the sensor to ensure a light-tight fit, a cord management system to provide strain relief and security from cord pulls, and a pull tab for easy removal of the attachment collar from the skin when the session is complete.

With reference to FIG. 21, the two-piece sensor comprises an attachment collar 2110 and a sensor 2120. Cable 2130 wraps around skin sensor 2020 and clips into cable management system 2140 to reduce cord pulls and provide strain relief. Pull table 2150 allows for easy removal from the skin of a patient after use.

Figure 22:
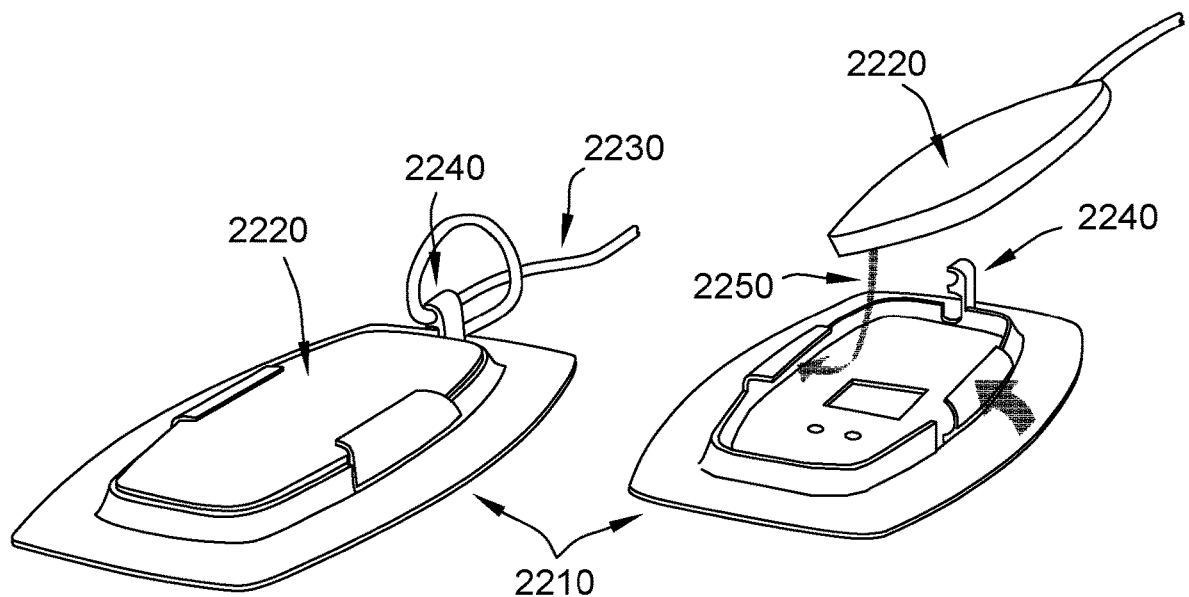
FIG. 22 illustrates one embodiment of the two-piece sensor assembly that includes clips on the skin sensor which secure the sensor to the attachment collar, a cord management system to provide strain relief and security from cord pulls, and a pull tab for easy removal of the attachment collar from the skin when the session is complete.

With reference to FIG. 22, the two-piece sensor comprises an attachment collar 2210 and a sensor 2220. Sensor 2220 slides under side table 2250 on the attachment collar 2210 to secure the sensor in place. Cable 2230 clips into cable management system 2240 to reduce cord pulls and provide strain relief. Pull table 2150 allows for easy removal from the skin of a patient after use.

In some aspects the attachment collar further comprises a means for securing the skin sensor to the at least one opening of the attachment collar as illustrated in FIGS. 1 to 22. In some aspects, the two-piece sensor assembly further comprises a means for managing a cable attached thereto as illustrated in FIGS. 1 to 22. In some aspects, the means for managing the cable is attached to the attachment collar, the skin sensor or both as illustrated in FIGS. 1 to 22. In some aspects, the skin sensor and/or the attachment collar further comprises a means of authentication between the skin sensor and the attachment collar as described elsewhere herein.

Indicator Substances

Suitable indicator substances for use with the methods and devices described herein are disclosed in U.S. 62/577,951, U.S. Pat. Nos. 8,155,000, 8,664,392, 8,697,033, 8,722,685, 8,778,309, 9,005,581, 9,114,160, 9,283,288, 9,376,399, and 9,480,687 which are all incorporated by reference in their entirety for all purposes. In some aspects, the indicator substance is eliminated from the body of a patient by glomerular filtration. In some aspects, the indicator substance is eliminated from the body of a patient only by glomerular filtration. In some aspects, the indicator substance is a GFR agent.

In some aspects, the indicator substance is a pyrazine derivative of Formula I, or a pharmaceutically acceptable salt thereof,

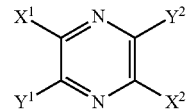

Formula I wherein each of $X^1$ and $X^2$ is independently selected from the group consisting of —CN, —CO$_2$R$^1$, —CONR$^1$R$^2$, —CO(AA), —CO(PS) and —CONH(PS); each of $Y^1$ and $Y^2$ is independently selected from the group consisting of —$NR^1R^2$ and

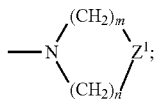

$Z^1$ is a single bond, —$CR^1R^2$—, —O—, —$NR^1$—, —$NCOR^1$—, —S—, —SO—, or —$SO_2$—; each of $R^1$ to $R^2$ are independently selected from the group consisting of H, —$CH_2(CHOH)_aH$, —$CH_2(CHOH)_aCH_3$, —$CH_2(CHOH)_aCO_2H$, —$(CHCO_2H)_aCO_2H$, —$(CH_2CH_2O)_cH$, —$(CH_2CH_2O)_cCH_3$, —$(CH_2)_aSO_3H$, —$(CH_2)_aSO_3^-$, —$(CH_2)_aSO_2H$, —$(CH_2)_aSO_2^-$, —$(CH_2)_aNHSO_3H$, —$(CH_2)_aNHSO_3^-$, —$(CH_2)_aNHSO_2H$, —$(CH_2)_aNHSO_2^-$, —$(CH_2)_aPO_4H_3$, —$(CH_2)_aPO_4H_2^-$, —$(CH_2)_aPO_4H^{2-}$, —$(CH_2)_aPO_4^{3-}$, —$(CH_2)_aPO_3H_2$, —$(CH_2)_aPO_3H^-$, and —$(CH_2)_aPO_3^{2-}$; (AA) comprises one or more amino acids selected from the group consisting of natural and unnatural amino acids, linked together by peptide or amide bonds and each instance of (AA) may be the same or different than each other instance; (PS) is a sulfated or non-sulfated polysaccharide chain that includes one or more monosaccharide units connected by glycosidic linkages; and 'a' is a number from 0 to 10, 'c' is a number from 1 to 100, and each of 'm' and 'n' are independently a number from 1 to 3. In another aspect, 'a' is a number from 1 to 10. In still yet another aspect, 'a' is 0, 1, 2, 3, 4, 5, 6, 7, 8, 9 or 10.

(AA) comprises one or more natural or unnatural amino acids linked together by peptide or amide bonds. The peptide chain (AA) may be a single amino acid, a homopolypeptide chain or a heteropolypeptide chain, and may be any appropriate length. In some embodiments, the natural or unnatural amino acid is an α-amino acid. In yet another aspect, the α-amino acid is a D-α-amino acid or an L-α-amino acid. In a polypeptide chain that includes two or more amino acids, each amino acid is selected independently of the other(s) in all aspects, including, but not limited to, the structure of the side chain and the stereochemistry. For example, in some embodiments, the peptide chain may include 1 to 100 amino acid(s), 1 to 90 amino acid(s), 1 to 80 amino acid(s), 1 to 70 amino acid(s), 1 to 60 amino acid(s), 1 to 50 amino acid(s), 1 to 40 amino acid(s), 1 to 30 amino acid(s), 1 to 20 amino acid(s), or even 1 to 10 amino acid(s). In some embodiments, the peptide chain may include 1 to 100 α-amino acid(s), 1 to 90 α-amino acid(s), 1 to 80 α-amino acid(s), 1 to 70 α-amino acid(s), 1 to 60 α-amino acid(s), 1 to 50 α-amino acid(s), 1 to 40 α-amino acid(s), 1 to 30 α-amino acid(s), 1 to 20 α-amino acid(s), or even 1 to 10 α-amino acid(s). In some embodiments, the amino acid is selected from the group consisting of D-alanine, D-arginine D-asparagine, D-aspartic acid, D-cysteine, D-glutamic acid, D-glutamine, glycine, D-histidine, D-homoserine, D-isoleucine, D-leucine, D-lysine, D-methionine, D-phenylalanine, D-proline, D-serine, D-threonine, D-tryptophan, D-tyrosine, and D-valine. In some embodiments, the α-amino acids of the peptide chain (AA) are selected from the group consisting of arginine, asparagine, aspartic acid, glutamic acid, glutamine, histidine, homoserine, lysine, and serine. In some embodiments, the α-amino acids of the peptide chain (AA) are selected from the group consisting of aspartic acid, glutamic acid, homoserine and serine. In some embodiments, the peptide chain (AA) refers to a single amino acid (e.g., D-aspartic acid or D-serine).

(PS) is a sulfated or non-sulfated polysaccharide chain including one or more monosaccharide units connected by glycosidic linkages. The polysaccharide chain (PS) may be any appropriate length. For instance, in some embodiments, the polysaccharide chain may include 1 to 100 monosaccharide unit(s), 1 to 90 monosaccharide unit(s), 1 to 80 monosaccharide unit(s), 1 to 70 monosaccharide unit(s), 1 to 60 monosaccharide unit(s), 1 to 50 monosaccharide unit(s), 1 to 40 monosaccharide unit(s), 1 to 30 monosaccharide unit(s), 1 to 20 monosaccharide unit(s), or even 1 to 10 monosaccharide unit(s). In some embodiments, the polysaccharide chain (PS) is a homopolysaccharide chain consisting of either pentose or hexose monosaccharide units. In other embodiments, the polysaccharide chain (PS) is a heteropolysaccharide chain consisting of one or both pentose and hexose monosaccharide units. In some embodiments, the monosaccharide units of the polysaccharide chain (PS) are selected from the group consisting of glucose, fructose, mannose, xylose and ribose. In some embodiments, the polysaccharide chain (PS) refers to a single monosaccharide unit (e.g., either glucose or fructose). In yet another aspect, the polysaccharide chain is an amino sugar where one or more of the hydroxy groups on the sugar has been replaced by an amine group. The connection to the carbonyl group can be either through the amine or a hydroxy group.

Specific examples of indicator substances include, but are not limited to, 3,6-diamino-$N^2,N^2,N^5,N^5$-tetrakis(2-methoxyethyl)pyrazine-2,5-dicarboxamide, 3,6-diamino-$N^2,N^5$-bis(2,3-dihydroxypropyl)pyrazine-2,5-dicarboxamide, (2S,2'S)-2,2'-((3,6-diaminopyrazine-2,5-dicarbonyl)bis(azanediyl))bis(3-hydroxypropanoic acid), 3,6-bis(bis(2-methoxyethyl)amino)-$N^2,N^2,N^5,N^5$-tetrakis(2-methoxyethyl) pyrazine-2,5-dicarboxamide bis(TFA) salt, 3,6-diamino-$N^2,N^5$-bis(2-aminoethyl)pyrazine-2,5-dicarboxamide bis(TFA) salt, 3,6-diamino-$N^2,N^5$-bis (D-aspartate)-pyrazine-2,5-dicarboxamide, 3,6-diamino-$N^2,N^5$-bis (14-oxo-2,5,8,11-tetraoxa-15-azaheptadecan-17-yl) pyrazine-2,5-dicarboxamide, 3,6-diamino-$N^2,N^5$-bis(26-oxo-2,5,8,11,14,17,20,23-octaoxa-27-azanonacosan-29-yl) pyrazine-2,5-dicarboxamide, 3,6-diamino-$N^2,N^5$-bis(38-oxo-2,5,8,11,14,17,20,23,26,29,32,35-dodecaoxa-39-azahentetracontan-41-yl)pyrazine-2,5-dicarboxamide, bis (2-(PEG-5000)ethyl) 6-(2-(3,6-diamino-5-(2-aminoethylcarbamoyl) pyrazine-2-carboxamido) ethylamino)-6-oxohexane-1,5-diyldicarbamate, (R)-2-(6-(bis(2-methoxyethyl)amino)-5-cyano-3-morpholinopyrazine-2-carboxamido)succinic acid, (2R, 2'R)-2,2'-((3,6-diaminopyrazine-2,5-dicarbonyl)bis (azanediyl))bis(3-hydroxypropanoic acid), (2S,2'S)-2,2'-((3, 6-diaminopyrazine-2,5-dicarbonyl)bis(azanediyl))bis(3-hydroxypropanoic acid), (2R,2'R)-2,2'-((3,6-diaminopyrazine-2,5-dicarbonyl)bis(azanediyl)) dipropionic acid, 3,3'-((3,6-diaminopyrazine-2,5-dicarbonyl)bis(azanediyl))dipropionic acid, 2,2'-((3,6-diaminopyrazine-2,5-dicarbonyl)bis(azanediyl))diacetic acid, (2S,2'S)-2, 2'-((3,6-diaminopyrazine-2,5-dicarbonyl)bis(azanediyl)) dipropionic acid, 2,2'-((3,6-diaminopyrazine-2,5-dicarbonyl)bis(azanediyl))bis(2-methylpropanoic acid), and 3,6-diamino-$N^2,N^5$-bis((1R,2S,3R,4R)-1,2,3,4,5-pentahydroxypentyl) pyrazine-2,5-dicarboxamide. In some aspects, the indicator substance is (2R,2'R)-2,2'-((3,6-diaminopyrazine-2,5-dicarbonyl)bis(azanediyl))bis(3-hydroxypropanoic acid) (also known as MB-102). In some aspects, the indicator substance is (2S,2'S)-2,2'-((3,6-diaminopyrazine-2,5-dicarbonyl)bis(azanediyl))bis(3-hydroxypropanoic acid).

In some aspects, the indicator substance is (2R,2'R)-2,2'-((3,6-diamino-pyrazine-2,5-dicarbonyl)bis(azanediyl))bis(3-hydroxypropanoic acid) (also known as MB-102 or 3,6-diamino-N2,N5-bis(D-serine)-pyrazine-2,5-dicarboxamide),

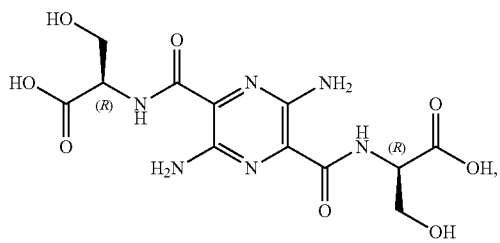

or a pharmaceutically acceptable salt thereof.

In some aspects, the indicator substance is (2S,2'S)-2,2'-((3,6-diamino-pyrazine-2,5-dicarbonyl)bis(azanediyl))bis(3-hydroxypropanoic acid) (also known as 3,6-diamino-N2,N5-bis(L-serine)-pyrazine-2,5-dicarboxamide),

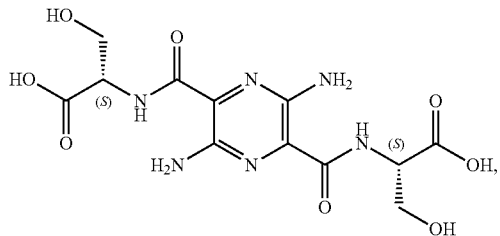

or a pharmaceutically acceptable salt thereof.

In still yet another aspect, the indicator substance is selected from the group consisting of acridines, acridones, anthracenes, anthracylines, anthraquinones, azaazulenes, azo azulenes, benzenes, benzimidazoles, benzofurans, benzoindocarbocyanines, benzoindoles, benzothiophenes, carbazoles, coumarins, cyanines, dibenzofurans, dibenzothiophenes, dipyrrolo dyes, flavones, imidazoles, indocarbocyanines, indocyanines, indoles, isoindoles, isoquinolines, naphthacenediones, naphthalenes, naphthoquinones, phenanthrenes, phenanthridines, phenanthridines, phenoselenazines, phenothiazines, phenoxazines, phenylxanthenes, polyfluorobenzenes, purines, pyrazines, pyrazoles, pyridines, pyrimidones, pyrroles, quinolines, quinolones, rhodamines, squaraines, tetracenes, thiophenes, triphenyl methane dyes, xanthenes, xanthones, and derivatives thereof. In still yet another aspect, the indicator substance is any compound that is eliminated from the body of a patient by glomerular filtration. In still yet another aspect, the indicator substance is any compound that emits fluorescent energy when exposed to electromagnetic radiation and is eliminated from the body of the patient by glomerular filtration.

In any aspect of the indicator substance, one or more atoms may alternatively be substituted with an isotopically labelled atom of the same element. For example, a hydrogen atom may be isotopically labelled with deuterium or tritium; a carbon atom may be isotopically labelled with $^{13}C$ or $^{14}C$; a nitrogen atom may be isotopically labelled with $^{14}N$ or $^{15}N$. An isotopic label may be a stable isotope or may be an unstable isotope (i.e., radioactive). The indicator substance may contain one or more isotopic labels. The isotopic label may be partial or complete. For example, an indicator substance may be labeled with 50% deuterium thereby giving the molecule a signature that can be readily monitored by mass spectroscopy or other technique. As another example, the indicator substance may be labeled with tritium thereby giving the molecule a radioactive signature that can be monitored both in vivo and ex vivo using techniques known in the art.

Pharmaceutically acceptable salts are known in the art. In any aspect herein, the indicator substance may be in the form of a pharmaceutically acceptable salt. By way of example and not limitation, pharmaceutically acceptable salts include those as described by Berge, et al. in *J. Pharm. Sci.*, 66(1), 1 (1977), which is incorporated by reference in its entirety for all purposes. The salt may be cationic or anionic. In some embodiments, the counter ion for the pharmaceutically acceptable salt is selected from the group consisting of acetate, benzenesulfonate, benzoate, besylate, bicarbonate, bitartrate, bromide, calcium edetate, camsylate, carbonate, chloride, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate, diphosphate, polygalacturonate, salicylate, stearate, subacetate, succinate, sulfate, tannate, tartrate, teoclate, triethiodide, adipate, alginate, aminosalicylate, anhydromethylenecitrate, arecoline, aspartate, bisulfate, butylbromide, camphorate, digluconate, dihydrobromide, disuccinate, glycerophosphate, jemisulfate, judrofluoride, judroiodide, methylenebis(salicylate), napadisylate, oxalate, pectinate, persulfate, phenylethylbarbarbiturate, picrate, propionate, thiocyanate, tosylate, undecanoate, benzathine, chloroprocaine, choline, diethanolamine, ethylenediamine, meglumine, procaine, benethamine, clemizole, diethylamine, piperazine, tromethamine, aluminum, calcium, lithium, magnesium, potassium, sodium zinc, barium and bismuth. Any functional group in the indicator substance capable of forming a salt may optionally form one using methods known in the art. By way of example and not limitation, amine hydrochloride salts may be formed by the addition of hydrochloric acid to the indicator substance. Phosphate salts may be formed by the addition of a phosphate buffer to the indicator substance. Any acid functionality present, such as a sulfonic acid, a carboxylic acid, or a phosphonic acid, may be deprotonated with a suitable base and a salt formed. Alternatively, an amine group may be protonated with an appropriate acid to form the amine salt. The salt form may be singly charged, doubly charged or even triply charged, and when more than one counter ion is present, each counter ion may be the same or different than each of the others.

In still yet another aspect, disclosed herein is a method for determining a glomerular filtration rate (GFR) in a patient in need thereof. The method generally comprises: applying a two-piece sensor assembly onto the body surface of the patient, administering into the body of the patient an indicator substance, said indicator substance configured to generate an optical response in response to an interrogation light; detecting said optical response using the two-piece sensor assembly over a predetermined period of time; and determining the GFR in said patient based on the detected optical response.

In some aspects of the method for determining the GFR in a patient, the two piece-sensor assembly is as described elsewhere herein. In some aspects of the method for determining the GFR in a patient, the indicator substance is as described elsewhere herein. In some aspects of the method for determining the GFR in a patient, the indicator substance is (2R,2'R)-2,2'-((3,6-diamino-pyrazine-2,5-dicarbonyl)bis-(azanediyl))bis(3-hydroxypropanoic acid) (also known as MB-102 or 3,6-diamino-N2,N5-bis(D-serine)-pyrazine-2,5-dicarboxamide),

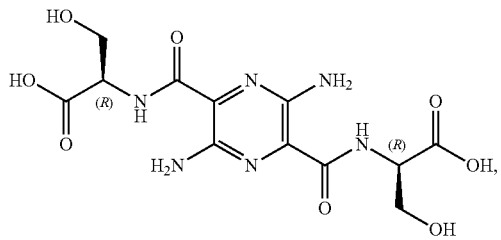

or a pharmaceutically acceptable salt thereof.

This written description uses examples to disclose the subject matter herein, including the best mode, and also to enable any person skilled in the art to practice the subject matter disclosed herein, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A two-piece sensor assembly comprising:
an attachment collar configured to attach to a body surface of a patient and comprising at least one opening,
a skin sensor configured to seat into the at least one opening in the attachment collar and comprising:
at least one radiation source configured to irradiate the body surface with at least one interrogation light, and
at least one detector configured to detect at least one response light incident from the direction of the body surface;
wherein the two-piece sensor assembly is configured to exert a positive pressure on the body surface directly beneath the skin sensor, while simultaneously applying a negative pressure to the body surface beneath or surrounding the attachment collar.

2. The two-piece sensor assembly according to claim 1, wherein
the attachment collar forms a light-tight seal with the body surface, and
the skin sensor forms a light-tight seal with the attachment collar.

3. The two-piece sensor assembly according to claim 1, further comprising
a controller communicatively coupled to the skin sensor, the attachment collar or both,
wherein the controller is programed to transmit information and to receive information between the controller and the skin sensor and/or the attachment collar, and to control the at least one radiation source and the at least one detector.

4. The two-piece sensor assembly according to claim 3, wherein the controller is further programmed to receive authentication information from the skin sensor, the attachment collar or both.

5. The two-piece sensor assembly according to claim 3, wherein the controller and the skin sensor are communicatively coupled using a cable connection, a wireless connection, or both.

6. The two-piece sensor assembly according to claim 1, wherein the attachment collar further comprises:
a locking mechanism configured to securely fasten the skin sensor to the at least one opening in the attachment collar.

7. The two-piece sensor assembly according to claim 1, wherein the two-piece sensor assembly further comprises:
a cable management system configured to reduce or eliminate accidental cord pulls that would dislodge or detach the two-piece sensor assembly from the body of the patient and/or reduce or eliminate accidental cord pulls that would dislodge or detach the skin sensor from the attachment collar, and
said cable management system is attached to the attachment collar, the skin sensor or both.

8. The two-piece sensor assembly according to claim 1, wherein the at least one response light is generated by an optical response from an indicator substance inside the body of the patient in response to the interrogation light.

9. The two piece sensor assembly according to claim 8, wherein the indicator substances is a molecule according to Formula I,

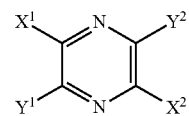

Formula I or a pharmaceutically acceptable salt thereof,
wherein
each of $X^1$ and $X^2$ is independently selected from the group consisting of —CN, —CO$_2$R$^1$, —CONR$^1$R$^2$, —CO(AA), —CO(PS) and —CONH(PS);
each of $Y^1$ and $Y^2$ is independently selected from the group consisting of —NR$^1$R$^2$ and

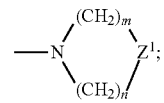

$Z^1$ is a single bond, —CR$^1$R$^2$—, —O—, —NR$^1$—, —NCOR$^1$—, —S—, —SO—, or —SO$_2$—; each of R$^1$ to R$^2$ are independently selected from the group consisting of H, —CH$_2$(CHOH)$_a$H, —CH$_2$(CHOH)$_a$CH$_3$, —CH$_2$(CHOH)$_a$CO$_2$H, —(CHCO$_2$H)$_a$CO$_2$H, —(CH$_2$CH$_2$O)$_c$H, —(CH$_2$CH$_2$O)$_c$CH$_3$, —(CH$_2$)$_a$SO$_3$H, —(CH$_2$)$_a$SO$_3$—, —(CH$_2$)$_a$SO$_2$H, —(CH$_2$)$_a$SO$_2$, —$(CH_2)_a NHSO_3 H$,   —$(CH_2)_a NHSO_3^-$,
—$(CH_2)_a NHSO_2 H$,   —$(CH_2)_a NHSO_2^-$,
—$(CH_2)_a PO_4 H_3$,   —$(CH_2)_a PO_4 H_2^-$,
—$(CH_2)_a PO_4 H^{2-}$, —$(CH_2)_a PO_4^{3-}$,
k—$(CH_2)_a PO_3 H_2$, —$(CH_2)_a PO_3 H^-$, and —$(CH_2)_a PO_3^{2-}$;

(AA) comprises one or more amino acids selected from the group consisting of natural and unnatural amino acids, linked together by peptide or amide bonds and each instance of (AA) may be the same or different than each other instance;

(PS) is a sulfated or non-sulfated polysaccharide chain that includes one or more monosaccharide units connected by glycosidic linkages;

'a' is a number from 0 to 10,

'c' is a number from 1 to 100, and each of 'm' and 'n' are independently a number from 1 to 3.

10. The two piece sensor assembly according to claim 8, wherein the indicator substances is

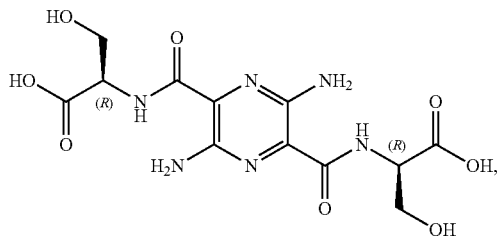

or a pharmaceutically acceptable salt thereof.

11. The two-piece sensor assembly according to claim 10, wherein the detector is configured to measure an intensity of the response light at a plurality of time points.

12. The two-piece sensor assembly according to claim 1, wherein the attachment collar comprises an elastomer.

13. The two-piece sensor assembly according to claim 12, wherein the elastomer is mixed with and/or comprises a layer of non-optically transmissive material.

14. The two-piece sensor assembly according to claim 13, wherein the non-optically transmissive material is graphite, carbon black, mylar, aluminum or a combination thereof.

15. The two-piece sensor assembly according to claim 1, wherein the attachment collar further comprises:
a means for securing the skin sensor to the at least one opening of the attachment collar.

16. The two-piece sensor assembly according to claim 1, wherein the two-piece sensor assembly further comprises:
a means for managing a cable attached thereto, and
the means for managing the cable is attached to the attachment collar, the skin sensor or both.

17. The two-piece sensor assembly according to claim 1, wherein the skin sensor and the attachment collar further comprises:
a means of authentication between the skin sensor and the attachment collar.

18. The two-piece sensor assembly according to claim 1, further comprises a two-sided adhesive; and
wherein the two-sided adhesive is configured to adhere to the skin of the patient on a first side and adhere to the skin sensor on a second side.

19. The two-piece sensor assembly according to claim 18, wherein the two-sided adhesive is a pressure activated adhesive that exhibits a stronger adhesive strength when placed under pressure as compared to the adhesive strength when not under pressure.

20. A method for determining a glomerular filtration rate (GFR) in a patient in need thereof, the method comprising:
applying the two-piece sensor assembly of claim 1 onto the body surface of the patient,
administering into the body of the patient an indicator substance, said indicator substance configured to generate an optical response in response to an interrogation light;
detecting said optical response using the two-piece sensor assembly over a predetermined period of time; and
determining the GFR in said patient based on the detected optical response.

* * * * *